(12) United States Patent
Dalmau et al.

(10) Patent No.: US 7,972,796 B2
(45) Date of Patent: Jul. 5, 2011

(54) METHODS FOR DIAGNOSIS OF ENCEPHALITIS

(75) Inventors: Josep Dalmau, Philadelphia, PA (US); Myrna Rosenfeld, Philadelphia, PA (US); David R. Lynch, Bleubell, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/277,252

(22) Filed: Nov. 24, 2008

(65) Prior Publication Data

US 2009/0155261 A1    Jun. 18, 2009

Related U.S. Application Data

(63) Continuation-in-part of application No. PCT/US2007/018092, filed on Aug. 15, 2007.

(60) Provisional application No. 60/837,624, filed on Aug. 15, 2006.

(51) Int. Cl.
*G01N 33/53* (2006.01)

(52) U.S. Cl. ...................................................... 435/7.1

(58) Field of Classification Search .................. None
See application file for complete search history.

(56) References Cited

PUBLICATIONS

Llansola et al. The Cerebellum 4: 154-161, 2005.*
Kalia et al. Lancet Neurol 7: 742-755, 2008.*
Sansing et al Nat Clin Practice Neurol 3: 291-296, 2007.*
Iizuka et al Neurol 70: pp. 504-511, 2008.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Kimura et al., Eur Neurol 58: 152-158, published online dated Jun. 29, 2007.*
Dunah et al Mol Neurobiol 19: 151-179, 1999.*
Gleichman et al. Soc Neurosc Meet Abst. No. 425.13/C25; Nov. 15-19, 2008.*

* cited by examiner

*Primary Examiner* — Daniel E Kolker
*Assistant Examiner* — Aditi Dutt
(74) *Attorney, Agent, or Firm* — Pearl Cohen Zedek Latzer, LLP; Mark S. Cohen

(57) ABSTRACT

This invention provides methods of diagnosing or determining a cause of an autoimmune encephalitis or an epilepsy in a subject and of diagnosing a tumor in a subject, comprising the step of testing a biological sample of the subject for an antibody to an NR1 subunit of the NMDA receptor. This invention further provides methods of treating an autoimmune encephalitis or an epilepsy, comprising the steps of detecting an antibody to an NR1 subunit of the NMDA receptor and treating a tumor associated with the disease.

7 Claims, 4 Drawing Sheets

METHODS FOR DIAGNOSIS OF ENCEPHALITIS

CROSS REFERENCE TO RELATED APPLICATIONS

This application is a Continuation-in-part Application of PCT Patent Application No. PCT/US2007/018092, filed Aug. 15, 2007, which claims priority to U.S. Provisional Patent Application No. 60/837,624, filed Aug. 15, 2006, now expired, both which are hereby incorporated by reference in their entirety.

FIELD OF INVENTION

This invention provides methods of diagnosing and treating an autoimmune encephalitis or an epilepsy in a subject using an antibody to an NR1 subunit of the NMDA receptor.

BACKGROUND OF THE INVENTION

Disturbances of memory, behavior, cognition, and seizures can result from immune-mediated encephalitis. One cause of autoimmune encephalitis is the paraneoplastic manifestation of a neoplasm. Most paraneoplastic encephalitides have been associated with antibodies to intracellular onconeuronal proteins and cytotoxic T-cells presumably against the same proteins. These disorders usually associate with malignant tumors and are poorly responsive to immunotherapies or treatment of the cancer.

In recent years, a severe but often reversible encephalitis of unknown etiology that predominantly affects young women has been increasingly recognized. The disorder has received several names, including acute diffuse lymphocytic meningoencephalitis, acute reversible limbic encephalitis, acute juvenile female non-herpetic encephalitis, or juvenile acute non-herpetic encephalitis. Since most patients develop a prodromic viral-like illness, a postinfectious immune-mediated etiology has been postulated.

The affected patients were women who developed prominent psychiatric symptoms, seizures, memory deficits, and decreased level of consciousness often requiring ventilatory support. Three salient features included the young age of the patients, the association with ovarian teratomas, and the detection of antibodies to unknown antigens predominantly expressed in the cell membrane of hippocampal neurons (also referred to as a subgroup of neuropil antigens).

A better understanding of the function of the paraneoplastic neuronal (or onconeuronal) antigens may help improve the treatment strategies. For the clinician who currently confronts these patients, however, the best chance to affect the neurologic outcome depends on: (1) the prompt diagnosis of the disorder, (2) the early discovery and treatment of the tumor, and (3) the use of immunotherapy. Accordingly, a need exists for reliable methods of diagnosing and treating autoimmune encephalitis or epileptic seizures.

SUMMARY OF THE INVENTION

In one embodiment, the present invention provides a method of diagnosing encephalitis in a subject, comprising the steps of obtaining a biological sample from the subject; and testing the biological sample for an antibody to an NR1 subunit of an NMDA receptor, whereby a presence of said antibody in said biological sample indicates an autoimmune encephalitis, thereby determining a cause of an encephalitis in a subject. In an exemplary embodiment, the NR1 subunit is a monomer of an NR multimer of an NMDA receptor.

In another embodiment, the present invention provides a method of diagnosing a tumor associated with an autoimmune encephalitis in a subject, comprising the steps of: obtaining a biological sample from the subject; and testing the biological sample for an antibody to an NR1 subunit of the NMDA receptor, whereby a presence of said antibody indicates a presence of an occult tumor in said subject and that said tumor is a cause of said autoimmune encephalitis.

In another embodiment, the present invention provides a method of diagnosing epilepsy in a subject, comprising the steps of: obtaining a biological sample from the subject; and testing the biological sample for the presence of an antibody to an NR1 subunit of the NMDA receptor, whereby a presence of said antibody indicates a presence of a tumor in said subject and said tumor is a cause of said epilepsy, thereby diagnosing epilepsy in a subject.

In another embodiment, the present invention provides a method of diagnosing a tumor in a subject having an epilepsy, comprising the step of: obtaining a biological sample from the subject; and testing the biological sample for the presence of an antibody to an NR1 subunit of the NMDA receptor, whereby a presence of said antibody indicates a presence of a tumor in said subject, thereby diagnosing a tumor in a subject having an epilepsy.

In another embodiment, the present invention provides a method of treating autoimmune encephalitis in a subject, comprising the steps of: detecting a tumor associated with an autoimmune encephalitis by testing a body fluid from the subject for an antibody to an NR1 subunit of the NMDA receptor, whereby a presence of said antibody indicates a presence of said tumor in said subject and that said tumor is a cause of said autoimmune encephalitis; and treating said tumor. In another embodiment, the tumor is treated within four months of the onset of a symptom associated with autoimmune encephalitis.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
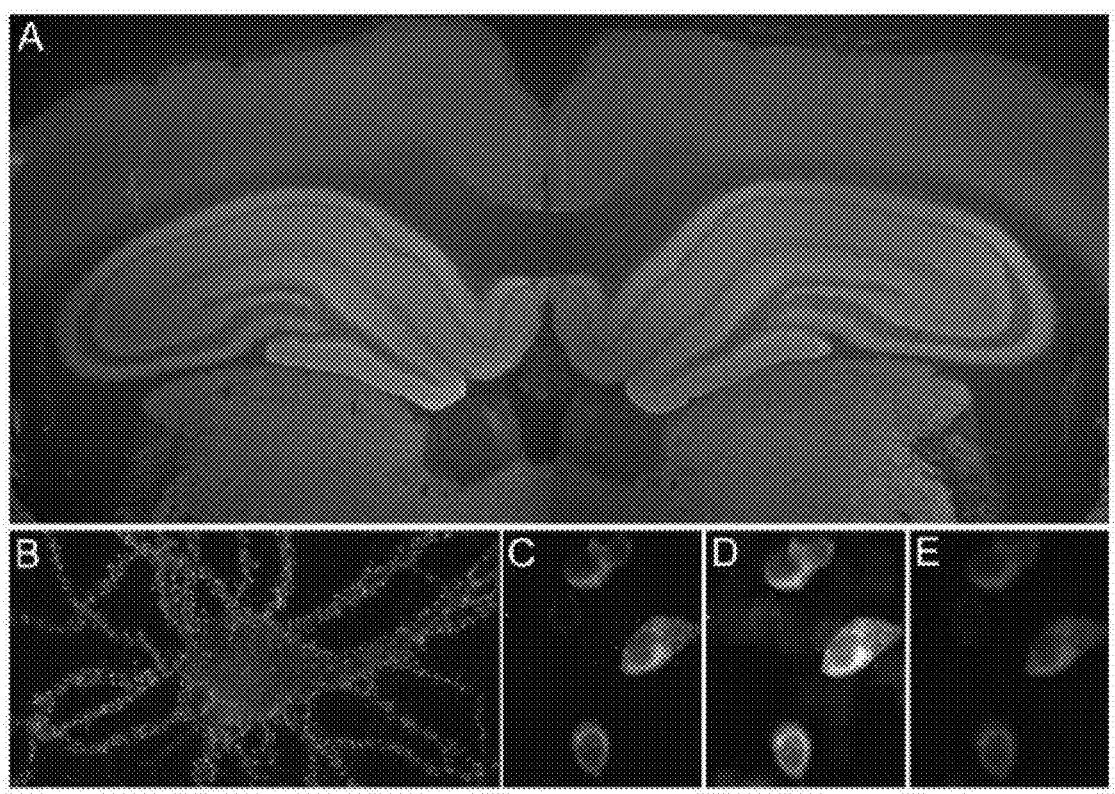
FIG. 1: Immunohistochemical criteria for the presence of NR1/NR2B antibodies. All patients' sera and CSF showed identical antibody reactivity demonstrated in three different assays. Coronal section of rat brain incubated with a representative CSF demonstrates intense reactivity predominantly involving the hippocampus (A). Cultures of non-permeabilized live rat hippocampal neurons incubated with the same CSF show extensive cell surface immunolabeling (B). HEK293 cells transfected with NR1 and NR2B (forming NR1/NR2B heteromers of the NMDA receptor) show intense reactivity with patient's CSF (C); this reactivity co-localizes (D) with the reactivity of a monoclonal rabbit antibody to NR1 (E). Immunofluorescence method, nuclei of cells demonstrated with 4',6-diamidino-2-phenylindole (DAPI). A ×25; B ×800 oil lens; C-E ×400.

This invention provides methods of diagnosing or determining a cause of an autoimmune encephalitis or an epilepsy in a subject and of diagnosing a tumor in a subject, comprising the step of testing a biological sample of the subject for an antibody to an NR1 subunit of the NMDA receptor.

In one embodiment, the present invention provides a method of determining a cause of an encephalitis in a subject, comprising the step of testing a body fluid of the subject for an antibody to an NR1 subunit of the NMDA receptor, thereby determining a cause of an encephalitis in a subject. In another embodiment, the presence of an antibody to an NR1 subunit in the body fluid indicates that the encephalitis is of autoimmune etiology. Each possibility represents a separate embodiment of the present invention.

In one embodiment, the methods and compositions provided herein facilitate the recognition of a severe form of autoimmune encephalitis that is often responsive to treatment. In another embodiment, the methods and compositions described herein emphasize the idea that autoimmunity can affect behavior, and particularly that an antibody to NR1 subunit of the NMDA receptor may alter emotion, in one embodiment, or memory, consciousness or their combination in other independent embodiments.

In another embodiment, the present invention provides a method of determining a cause of an autoimmune encephalitis in a subject, comprising the step of testing a body fluid of the subject for an antibody to an NR1 subunit of the NMDA receptor, thereby determining a cause of an autoimmune encephalitis in a subject. In another embodiment, the presence of the antibody indicates a presence of a tumor in the subject. In another embodiment, the tumor is a cause of the autoimmune encephalitis. Each possibility represents a separate embodiment of the present invention.

In another embodiment, the present invention provides a method of diagnosing an autoimmune encephalitis in a subject, comprising the step of testing a body fluid of the subject for an antibody to an NR1 subunit of the NMDA receptor, thereby diagnosing an autoimmune encephalitis in a subject.

In another embodiment, the present invention provides a method of diagnosing a paraneoplastic autoimmune encephalitis in a subject, comprising the step of testing a body fluid of the subject for an antibody to an NR1 subunit of the NMDA receptor, thereby diagnosing a paraneoplastic autoimmune encephalitis in a subject.

The biological sample used in the methods described herein is a body fluid that is tested by methods of the present invention is, in another embodiment, a cerebro-spinal fluid (CSF). In another embodiment, the body fluid is plasma. In another embodiment, the body fluid is any other type of fluid known in the art. Each possibility represents a separate embodiment of the present invention. In another embodiment, the biological sample is amniotic fluids, blood, sera, saliva, or their combination in another embodiment.

The autoimmune encephalitis of methods and compositions of the present invention is, in another embodiment, an autoimmune encephalitis. In another embodiment, the autoimmune encephalitis is a paraneoplastic encephalitis. In another embodiment, the autoimmune encephalitis is a non-paraneoplastic encephalitis. In another embodiment, the autoimmune encephalitis is a paraneoplastic autoimmune encephalitis. In another embodiment, the autoimmune encephalitis is a non-paraneoplastic, autoimmune encephalitis. In another embodiment, the autoimmune encephalitis is any other type of autoimmune encephalitis known in the art. Each possibility represents a separate embodiment of the present invention.

In one embodiment, the frequency of paraneoplastic anti-NMDAR encephalitis, diagnosed by the methods described herein, is unknown. In another embodiment paraneoplastic anti-NMDAR encephalitis is frequently unrecognized. This may be due to several features that make this disorder unique among paraneoplastic encephalitis, including in one embodiment, involvement of relatively young women between the $2^{nd}$ and $5^{th}$ decades, or, in another embodiment, the unusual presentation with prominent psychiatric manifestations, or in another embodiment, normal or atypical MRI findings, which in 75% of cases consist of mild, transient T2 or FLAIR abnormalities outside the medial temporal lobes, with cortical enhancement in certain embodiments, or in yet another embodiment, the benign appearance of the ovarian tumors. In one embodiment, any of the subjects presenting the symptoms described hereinabove are diagnosed using the methods described herein.

Anti-NMDAR encephalitis is different from other types of paraneoplastic encephalitis in several ways: it results in a highly characteristic syndrome; usually affects young women; is treatment-responsive; and associates with tumors that can be benign. Another difference shown here is that despite the presence of the tumor, the immune response is not maintained. This brings into consideration a contributory role of the prodromal "viral-like" disorder, which by itself or in combination with a teratoma sets off or enhances the autoimmune response. In one embodiment, the methods provided herein are used to differentiate anti-NMDAR encephalitis from other types of paraneoplastic encephalitis.

In another embodiment, the autoimmune encephalitis is a limbic encephalitis. In another embodiment, the autoimmune encephalitis is associated with a limbic dysfunction. In another embodiment, the autoimmune encephalitis is not associated with a limbic dysfunction. Each possibility represents a separate embodiment of the present invention.

In one embodiment, limbic encephalitis causes impressive deficits that are characteristically dominated by rapid and severe loss of short-term memory. In another embodiment, patients show subacute encephalitis of later adult life, mainly affecting the limbic areas with evidence of cancer in one embodiment. In one embodiment, the term "limbic encephalitis" refers to a subject exhibiting severe short-term memory loss and dementia in association with bronchial carcinoma.

In another embodiment, the autoimmune encephalitis of methods and compositions of the present invention is associated with seizures. In another embodiment, the autoimmune encephalitis is associated with a diencephalic syndrome. In another embodiment, the autoimmune encephalitis is associated with a psychiatric symptom. In another embodiment, the autoimmune encephalitis is associated with an abnormality in cognition. In another embodiment, the autoimmune encephalitis is associated with an abnormality in behavior.

In another embodiment, the autoimmune encephalitis is associated with amnesia. In another embodiment, the autoimmune encephalitis is associated with a memory deficit. In another embodiment, the autoimmune encephalitis is associated with memory problems. In another embodiment, the autoimmune encephalitis is associated with a hypokinetic syndrome.

In another embodiment, the autoimmune encephalitis is associated with a movement disorder. In another embodiment, the autoimmune encephalitis is associated with abnormal movements. In another embodiment, the movement disorder is Stiff Man/Person Syndrome. In another embodiment, the movement disorder is any other movement disorder known in the art. Each possibility represents a separate embodiment of the present invention.

In another embodiment, the autoimmune encephalitis is associated with a decreased level of consciousness. In another embodiment, the autoimmune encephalitis is associated with hypoventilation.

In another embodiment, the autoimmune encephalitis is associated with, dysfunction of any part of the brain or spinal cord. In another embodiment, the autoimmune encephalitis is associated with a combination of any of the above symptoms or disorders. Each type of encephalitis represents a separate embodiment of the present invention.

In another embodiment, the autoimmune encephalitis is associated with a tumor. In another embodiment, the tumor is an ovarian teratoma. In another embodiment, the tumor is a thymic tumor.

In another embodiment, the tumor is a testicular tumor. In another embodiment, the cancer associated with the encephalitis is a cervical cancer tumor. In another embodiment, the cancer is a head and neck cancer tumor. In another embodiment, the cancer is a breast cancer tumor. In another embodiment, the cancer is an ano-genital cancer tumor.

In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is mesothelioma. In another embodiment, the cancer is a glioma. In another embodiment, the cancer is a germ cell tumor. In another embodiment, the cancer is a choriocarcinoma. Each possibility represents a separate embodiment of the present invention.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma.

In another embodiment, the tumor is any other type of tumor known in the art. Each possibility represents a separate embodiment of the present invention.

In another embodiment, the present invention provides a method of determining a cause of an epilepsy in a subject, comprising the step of testing a body fluid of the subject for an antibody to an antibody to an NR1 subunit of the NMDA receptor, thereby determining a cause of an epilepsy in a subject. In another embodiment, the antibody indicates a presence of a tumor in the subject. In another embodiment, the tumor is a cause of the epilepsy. Each possibility represents a separate embodiment of the present invention.

The epilepsy of methods and compositions of the present invention is, in another embodiment, an idiopathic epilepsy. In another embodiment, the epilepsy responds to IgG-depleting therapy. In another embodiment, the epilepsy is associated with partial seizures. In another embodiment, the epilepsy is associated with simple partial seizures. In another embodiment, the epilepsy is associated with complex partial seizures. In another embodiment, the epilepsy is associated with generalized seizures. In another embodiment, the epilepsy is associated with absence (petit mal) seizures. In another embodiment, the epilepsy is associated with myoclonic seizures. In another embodiment, the epilepsy is associated with tonic-clonic (grand mal) seizures.

In another embodiment, the epilepsy is associated with West syndrome. In another embodiment, the epilepsy is associated with Lennox-Gastaut syndrome. In another embodiment, the epilepsy is associated with any other syndrome known in the art.

In another embodiment the epilepsy is of no known cause. In another embodiment the epilepsy is any other type of epilepsy known in the art. Each type of epilepsy represents a separate embodiment of the present invention.

"Cause of" an autoimmune encephalitis, epilepsy, etc, refers, in another embodiment, to a primary cause of the disorder. In another embodiment, the term refers to a contributing cause of the disorder. In another embodiment, the term refers to an indirect causation. In another embodiment, the term refers to causation via an immune response induced by the tumor. In another embodiment, the term refers to a significant cause of the disorder. Each possibility represents a separate embodiment of the present invention.

In another embodiment, the present invention provides a method of diagnosing a tumor in a subject having an encephalitis, comprising the step of testing a body fluid of the subject for an antibody to an NR1 subunit of the NMDA receptor, thereby diagnosing a tumor in a subject having an encephalitis. In another embodiment, the presence of the antibody indicates a presence of a tumor in the subject. Each possibility represents a separate embodiment of the present invention.

In another embodiment, the present invention provides a method of detecting a tumor in a subject having an encephalitis, comprising the step of testing a body fluid of the subject for an antibody to an NR1 subunit of the NMDA receptor, thereby detecting a tumor in a subject having an encephalitis. In another embodiment, the presence of the antibody indicates a presence of a tumor in the subject. Each possibility represents a separate embodiment of the present invention.

In one embodiment, the present invention provides a method of diagnosing a tumor in a subject having an epilepsy, comprising the step of testing a body fluid of the subject for an antibody to an antibody to an NR1 subunit of the NMDA receptor, thereby diagnosing a tumor in a subject having an epilepsy. In another embodiment, the presence of the antibody indicates a presence of a tumor in the subject. Each possibility represents a separate embodiment of the present invention.

In one embodiment, the present invention provides a method of detecting a tumor in a subject having an epilepsy, comprising the step of testing a body fluid of the subject for an antibody to an antibody to an NR1 subunit of the NMDA (N-methyl D-aspartate) receptor, thereby detecting a tumor in a subject having an epilepsy. In another embodiment, the presence of the antibody indicates a presence of a tumor in the subject. Each possibility represents a separate embodiment of the present invention.

In one embodiment, the invention provides a method of treating autoimmune encephalitis in a subject. In one embodiment, the method comprises the steps of: detecting a tumor associated with an autoimmune encephalitis by testing a body fluid from the subject for an antibody to an NR1 subunit of the NMDA receptor, whereby a presence of said antibody indicates a presence of said tumor in said subject and that said tumor is a cause of said autoimmune encephalitis. In another embodiment, the method comprises the step of treating said tumor. In another embodiment, the tumor is treated during the early stage. In another embodiment, the tumor is treated within four months of the onset of a symptom associated with autoimmune encephalitis. In another embodiment, the tumor is treated within three months of the onset of a symptom associated with autoimmune encephalitis. In another embodiment, the tumor is treated within two months of the onset of a symptom associated with autoimmune encephalitis. In another embodiment, the tumor is treated within one month of the onset of a symptom associated with autoimmune encephalitis.

In one embodiment, the step of treating said tumor comprises removing said tumor. In another embodiment, the step of treating said tumor comprises immunotherapy. In another embodiment, the step of treating said tumor comprises removing said tumor in combination with immunotherapy.

In one embodiment, NMDARs comprise subunits. In another embodiment, NMDARs are formed from heteromers of NR1 (which bind glycine) and NR2 subunits (which bind glutamate). In another embodiment, both subunits are required to create a functional receptor that contains NR1 and NR2 subunits. NR1 is ubiquitously distributed in the brain. With maturity many NR1/NR2B receptors become largely extrasynaptic in hippocampal neurons and NR1/NR2A/NR2B becomes the major synaptic receptors in the hippocampus and forebrain. Thus, in one embodiment, the predominant reactivity of the subjects' antibodies with hippocampus and forebrain correlates with the distribution of heteromers containing NR1. In one embodiment, the antibodies readily access cells surface epitopes of live neurons, and only react with HEK293 cells expressing functional receptors, for example, NR1 subunit of NMDA receptor.

The NR subunit of methods and compositions of the present invention is, in another embodiment, a NR1 subunit. In another embodiment, the NR subunit binds glycine. In another embodiment, NMDA receptor is a ligand-gated cation channel with critical roles in synaptic transmission and plasticity. In another embodiment, the receptor exists as heteromers of NR1 subunits that bind glycine, and NR2 (A, B, C or D) subunits that bind glutamate. In one embodiment, NR1 and NR2 combine to form receptor subtypes with distinct pharmacological properties, localization, and ability to interact with intracellular messengers. In another embodiment, overactivity of NMDA receptors causing excitotoxicity is a proposed mechanism in epilepsy, dementia, and stroke, while hypofunction produces symptoms of schizophrenia.

In another embodiment, the NR1 subunit is a monomer of an NR multimer of an NMDA receptor. In another embodiment, the NR multimer is a homomer that comprises two or more NR1 subunits. In another embodiment, the NR multimer is a homo-dimer that comprises two NR1 subunits. In another embodiment, the NR multimer is a heteromer that comprises an NR1 subunit. In another embodiment, the NR multimer is a heteromer that comprises an NR1 subunit and an NR2 subunit. In another embodiment, the NR multimer is a heteromer that comprises an NR1 subunit and an NR2A subunit. In another embodiment, the NR multimer is a heteromer that comprises an NR1 subunit and an NR2B subunit. In another embodiment, the NR multimer is a heteromer that comprises an NR1 subunit and an NR2C subunit. In another embodiment, the NR multimer is a heteromer that comprises an NR1 subunit and an NR2D subunit.

In one embodiment, the NR1 subunit has the sequence of NR1-3:

```
                                                              (SEQ ID NO: 1)
MSTMRLLTLALLFSCSVARAACDPKIVNIGAVLSTRKHEQMFREAVNQANKRHGSWKIQLNATSVTHKPN

AIQMALSVCEDLISSQVYAILVSHPPTPNDHFTPTPVSYTAGFYRIPVLGLTTRMSIYSDKSIHLSFLRT

VPPYSHQSSVWFEMMRVYSWNHIILLVSDDHEGRAAQKRLETLLEERESKAEKVLQFDPGTKNVTALLME

AKELEARVIILSASEDDAATVYRAAAMLNMTGSGYVWLVGEREISGNALRYAPDGILGLQLINGKNESAH

ISDAVGVVAQAVHELLEKENITDPPRGCVGNTNIWKTGPLFKRVLMSSKYADGVTGRVEFNEDGDRKFAN

YSIMNLQNRKLVQVGIYNGTHVIPNDRKIIWPGGETEKPRGYQMSTRLKIVTIHQEPFVYVKPTLSDGTC

KEEFTVNGDPVKKVICTGPNDTSPGSPRHTVPQCCYGFCIDLLIKLARTMNFTYEVHLVADGKFGTQERV

NNSNKKEWNGMMGELLSGQADMIVAPLTINNERAQYIEFSKPFKYQGLTILVKKEIPRSTLDSFMQPFQS

TLWLLVGLSVHVVAVMLYLLDRFSPFGRFKVNSEEEEEDALTLSSAMWFSWGVLLNSGIGEGAPRSFSAR

ILGMVWAGFAMIIVASYTANLAAFLVLDRPEERITGINDPRLRNPSDKFIYATVKQSSVDIYFRRQVELS

TMYRHMEKHNYESAAEAIQAVRDNKLHAFIWDSAVLEFEASQKCDLVTTGELFFRSGFGIGMRKDSPWKQ

NVSLSILKSHENGFMEDLDKTWVRYQECDSRSNAPATLTFENMAGVFMLVAGGIVAGIFLIFIEIAYKRH

KDARRKQMQLAFAAVNVWRKNLQDRKSGRAEPDPKKKATFRAITSTLASSFKRRRSSKDTSTGGGRGALQ

NQKDTVLPRRAIEREEGQLQLCSRHRES
```

In another embodiment, the NR1 subunit has the sequence of NR1-2:

```
                                                              (SEQ ID NO: 2)
MSTMRLLTLALLFSCSVARAACDPKIVNIGAVLSTRKHEQMFREAVNQANKRHGSWKIQLNATSVTHKPN

AIQMALSVCEDLISSQVYAILVSHPPTPNDHFTPTPVSYTAGFYRIPVLGLTTRMSIYSDKSIHLSFLRT

VPPYSHQSSVWFEMMRVYSWNHIILLVSDDHEGRAAQKRLETLLEERESKAEKVLQFDPGTKNVTALLME

AKELEARVIILSASEDDAATVYRAAAMLNMTGSGYVWLVGEREISGNALRYAPDGILGLQLINGKNESAH

ISDAVGVVAQAVHELLEKENITDPPRGCVGNTNIWKTGPLFKRVLMSSKYADGVTGRVEFNEDGDRKFAN

YSIMNLQNRKLVQVGIYNGTHVIPNDRKIIWPGGETEKPRGYQMSTRLKIVTIHQEPFVYVKPTLSDGTC

KEEFTVNGDPVKKVICTGPNDTSPGSPRHTVPQCCYGFCIDLLIKLARTMNFTYEVHLVADGKFGTQERV

NNSNKKEWNGMMGELLSGQADMIVAPLTINNERAQYIEFSKPFKYQGLTILVKKEIPRSTLDSFMQPFQS

TLWLLVGLSVHVVAVMLYLLDRFSPFGRFKVNSEEEEEDALTLSSAMWFSWGVLLNSGIGEGAPRSFSAR

ILGMVWAGFAMIIVASYTANLAAFLVLDRPEERITGINDPRLRNPSDKFIYATVKQSSVDIYFRRQVELS

TMYRHMEKHNYESAAEAIQAVRDNKLHAFIWDSAVLEFEASQKCDLVTTGELFFRSGFGIGMRKDSPWKQ

NVSLSILKSHENGFMEDLDKTWVRYQECDSRSNAPATLTFENMAGVFMLVAGGIVAGIFLIFIEIAYKRH

KDARRKQMQLAFAAVNVWRKNLQSTGGGRGALQNQKDTVLPRRAIEREEGQLQLCSRHRES
```

In another embodiment, the NR1 subunit has the sequence of NR1-1:

```
                                                       (SEQ ID NO: 3)
MSTMRLLTLALLFSCSVARAACDPKIVNIGAVLSTRKHEQMFREAVNQANKRHGSWKIQLNATSVTHKPN

AIQMALSVCEDLISSQVYAILVSHPPTPNDHFTPTPVSYTAGFYRIPVLGLTTRMSIYSDKSIHLSFLRT

VPPYSHQSSVWFEMMRVYSWNHIILLVSDDHEGRAAQKRLETLLEERESKAEKVLQFDPGTKNVTALLME

AKELEARVIILSASEDDAATVYRAAAMLNMTGSGYVWLVGEREISGNALRYAPDGILGLQLINGKNESAH

ISDAVGVVAQAVHELLEKENITDPPRGCVGNTNIWKTGPLFKRVLMSSKYADGVTGRVEFNEDGDRKFAN

YSIMNLQNRKLVQVGIYNGTHVIPNDRKIIWPGGETEKPRGYQMSTRLKIVTIHQEPFVYVKPTLSDGTC

KEEFTVNGDPVKKVICTGPNDTSPGSPRHTVPQCCYGFCIDLLIKLARTMNFTYEVHLVADGKFGTQERV

NNSNKKEWNGMMGELLSGQADMIVAPLTINNERAQYIEFSKPFKYQGLTILVKKEIPRSTLDSFMQPFQS

TLWLLVGLSVHVVAVMLYLLDRFSPFGRFKVNSEEEEEDALTLSSAMWFSWGVLLNSGIGEGAPRSFSAR

ILGMVWAGFAMIIVASYTANLAAFLVLDRPEERITGINDPRLRNPSDKFIYATVKQSSVDIYFRRQVELS

TMYRHMEKHNYESAAEAIQAVRDNKLHAFIWDSAVLEFEASQKCDLVTTGELFFRSGFGIGMRKDSPWKQ

NVSLSILKSHENGFMEDLDKTWVRYQECDSRSNAPATLTFENMAGVFMLVAGGIVAGIFLIFIEIAYKRH

KDARRKQMQLAFAAVNVWRKNLQQYHPTDITGPLNLSDPSVSTVV
```

In another embodiment, the NR1 subunit is a homologue of SEQ ID NOs: 1, 2, or 3. In another embodiment, the NR1 subunit is a variant of SEQ ID NOs: 1, 2, or 3. In another embodiment, the NR1 subunit is an isomer of SEQ ID NOs: 1, 2, or 3. In another embodiment, the NR1 subunit is a fragment of SEQ ID NOs: 1, 2, or 3. In another embodiment, the NR1 subunit comprises SEQ ID NOs: 1, 2, or 3. Each possibility represents a separate embodiment of the present invention.

In another embodiment, the NR1-3 is encoded by a nucleotide sequence having the sequence:

```
                                                       (SEQ ID NO: 4)
GTCGCCGCAGCGTCCGGACCGGAACCAGCGCCGTCCGCGGAGCCGCCGCCGCCGCCGGGCCCTTTCC

AAGCCGGGCGCTCGGAGCTGTGCCCGGCCCCGCTTCAGCACCGCGGACAGCGCCGGCCGCGTGGGGCTGA

GCCCCGAGCCCCCGCGCACGCTTCAGCGCCCCTTCCCTCGGCCGACGTCCCGGGACCGCCGCTCCGGGGG

AGACGTGGCGTCCGCAGCCCGCGGGGCCGGGCGAGCGCAGGACGGCCCGGAAGCCCCGCGGGGGATGCGC

CGAGGGCCCCGCGTTCGCGCCGCGCAGAGCCAGGCCCGCGGCCCGAGCCCATGAGCACCATGCGCCTGCT

GACGCTCGCCCTGCTGTTCTCCTGCTCCGTCGCCCGTGCCGCGTGCGACCCCAAGATCGTCAACATTGGC

GCGGTGCTGAGCACGCGGAAGCACGAGCAGATGTTCCGCGAGGCCGTGAACCAGGCCAACAAGCGGCACG

GCTCCTGGAAGATTCAGCTCAATGCCACCTCCGTCACGCACAAGCCCAACGCCATCCAGATGGCTCTGTC

GGTGTGCGAGGACCTCATCTCCAGCCAGGTCTACGCCATCCTAGTTAGCCATCCACCTACCCCCAACGAC

CACTTCACTCCCACCCCTGTCTCCTACACAGCCGGCTTCTACCGCATACCCGTGCTGGGGCTGACCACCC

GCATGTCCATCTACTCGGACAAGAGCATCCACCTGAGCTTCCTGCGCACCGTGCCGCCCTACTCCCACCA

GTCCAGCGTGTGGTTTGAGATGATGCGTGTCTACAGCTGGAACCACATCATCCTGCTGGTCAGCGACGAC

CACGAGGGCCGGGCGGCTCAGAAACGCCTGGAGACGCTGCTGGAGGAGCGTGAGTCCAAGGCAGAGAAGG

TGCTGCAGTTTGACCCAGGGACCAAGAACGTGACGGCCCTGCTGATGGAGGCGAAAGAGCTGGAGGCCCG

GGTCATCATCCTTTCTGCCAGCGAGGACGATGCTGCCACTGTATACCGCGCAGCCGCGATGCTGAACATG

ACGGGCTCCGGGTACGTGTGGCTGGTCGGCGAGCGCGAGATCTCGGGGAACGCCCTGCGCTACGCCCCAG

ACGGCATCCTCGGGCTGCAGCTCATCAACGGCAAGAACGAGTCGGCCCACATCAGCGACGCCGTGGGCGT

GGTGGCCCAGGCCGTGCACGAGCTCCTCGAGAAGGAGAACATCACCGACCCGCCGCGGGGCTGCGTGGGC

AACACCAACATCTGGAAGACCGGGCCGCTCTTCAAGAGAGTGCTGATGTCTTCCAAGTATGCGGATGGGG

TGACTGGTCGCGTGGAGTTCAATGAGGATGGGGACCGGAAGTTCGCCAACTACAGCATCATGAACCTGCA
```

-continued

```
GAACCGCAAGCTGGTGCAAGTGGGCATCTACAATGGCACCCACGTCATCCCTAATGACAGGAAGATCATC

TGGCCAGGCGGAGAGACAGAGAAGCCTCGAGGGTACCAGATGTCCACCAGACTGAAGATTGTGACGATCC

ACCAGGAGCCCTTCGTGTACGTCAAGCCCACGCTGAGTGATGGGACATGCAAGGAGGAGTTCACAGTCAA

CGGCGACCCAGTCAAGAAGGTGATCTGCACCGGGCCAACGACACGTCGCCGGGCAGCCCCCGCCACACG

GTGCCTCAGTGTTGCTACGGCTTTTGCATCGACCTGCTCATCAAGCTGGCACGGACCATGAACTTCACCT

ACGAGGTGCACCTGGTGGCAGATGGCAAGTTCGGCACACAGGAGCGGGTGAACAACAGCAACAAGAAGGA

GTGGAATGGGATGATGGGCGAGCTGCTCAGCGGGCAGGCAGACATGATCGTGGCGCCGCTAACCATAAAC

AACGAGCGCGCGCAGTACATCGAGTTTTCCAAGCCCTTCAAGTACCAGGGCCTGACTATTCTGGTCAAGA

AGGAGATTCCCCGGAGCACGCTGGACTCGTTCATGCAGCCGTTCCAGAGCACACTGTGGCTGCTGGTGGG

GCTGTCGGTGCACGTGGTGGCCGTGATGCTGTACCTGCTGGACCGCTTCAGCCCCTTCGGCCGGTTCAAG

GTGAACAGCGAGGAGGAGGAGGAGGACGCACTGACCCTGTCCTCGGCCATGTGGTTCTCCTGGGGCGTCC

TGCTCAACTCCGGCATCGGGGAAGGCGCCCCCAGAAGCTTCTCAGCGCGCATCCTGGGCATGGTGTGGGC

CGGCTTTGCCATGATCATCGTGGCCTCCTACACCGCCAACCTGGCGGCCTTCCTGGTGCTGGACCGGCCG

GAGGAGCGCATCACGGGCATCAACGACCCTCGGCTGAGGAACCCCTCGGACAAGTTTATCTACGCCACGG

TGAAGCAGAGCTCCGTGGATATCTACTTCCGGCGCCAGGTGGAGCTGAGCACCATGTACCGGCATATGGA

GAAGCACAACTACGAGAGTGCGGCGGAGGCCATCCAGGCCGTGAGAGACAACAAGCTGCATGCCTTCATC

TGGGACTCGGCGGTGCTGGAGTTCGAGGCCTCGCAGAAGTGCGACCTGGTGACGACTGGAGAGCTGTTTT

TCCGCTCGGGCTTCGGCATAGGCATGCGCAAAGACAGCCCCTGGAAGCAGAACGTCTCCCTGTCCATCCT

CAAGTCCCACGAGAATGGCTTCATGGAAGACCTGGACAAGACGTGGGTTCGGTATCAGGAATGTGACTCG

CGCAGCAACGCCCCTGCGACCCTTACTTTTGAGAACATGGCCGGGGTCTTCATGCTGGTAGCTGGGGGCA

TCGTGGCCGGGATCTTCCTGATTTTCATCGAGATTGCCTACAAGCGGCACAAGGATGCTCGCCGGAAGCA

GATGCAGCTGGCCTTTGCCGCCGTTAACGTGTGGCGGAAGAACCTGCAGGATAGAAAGAGTGGTAGAGCA

GAGCCTGACCCTAAAAAGAAAGCCACATTTAGGGCTATCACCTCCACCCTGGCTTCCAGCTTCAAGAGGC

GTAGGTCCTCCAAAGACACGAGCACCGGGGGTGGACGCGGCGCTTTGCAAAACCAAAAAGACACAGTGCT

GCCGCGACGCGCTATTGAGAGGGAGGAGGGCCAGCTGCAGCTGTGTTCCCGTCATAGGGAGAGCTGAGAC

TCCCCGCCCGCCCTCCTCTGCCCCCTCCCCCGCAGACAGACAGACGACGGACGGGACAGCGGCCCGGCC

CACGCAGAGCCCCGGAGCACCACGGGGTCGGGGGAGGAGCACCCCCAGCCTCCCCCAGGCTGCGCCTGCC

CGCCCGCCGGTTGGCCGGCTGGCCGGTCCACCCCGTCCCGGCCCCGCGCGTGCCCCCAGCGTGGGGCTAA

CGGGCGCCTTGTCTGTGTATTTCTATTTTGCAGCAGTACCATCCCACTGATATCACGGGCCCGCTCAACC

TCTCAGATCCCTCGGTCAGCACCGTGGTGTGAGGCCCCCGGAGGCGCCCACCTGCCCAGTTAGCCCGGCC

AAGGACACTGATGGGTCCTGCTGCTCGGGAAGGCCTGAGGGAAGCCCACCCGCCCCAGAGACTGCCCACC

CTGGGCCTCCCGTCCGTCCGCCCGCCCACCCCGCTGCCTGGCGGGCAGCCCCTGCTGGACCAAGGTGCGG

ACCGGAGCGGCTGAGGACGGGGCAGAGCTGAGTCGGCTGGGCAGGCCGCAGGGCGCTCCGGCAGAGGCA

GGGCCCTGGGGTCTCTGAGCAGTGGGGAGCGGGGCTAACTGGCCCCAGGCGGAGGGGCTTGGAGCAGAG

ACGGCAGCCCCATCCTTCCCGCAGCACCAGCCTGAGCCACAGTGGGGCCCATGGCCCCAGCTGGCTGGGT

CGCCCCTCCTCGGGCGCCTGCGCTCCTCTGCAGCCTGAGCTCCACCCTCCCCTCTTCTTGCGGCACCGCC

CACCCACACCCCGTCTGCCCCTTGACCCCACACGCCGGGGCTGGCCCTGCCCTCCCCACGGCCGTCCCT

GACTTCCCAGCTGGCAGCGCCTCCCGCCGCCTCGGGCCGCCTCCTCCAGACTCGAGAGGGCTGAGCCCCT

CCTCTCCTCGTCCGGCCTGCAGCCCAGAACGGGCCTCCCCGGGGGTCCCCGGACGCTGGCTCGGGACTGT

CTTCAACCCTGCCCTGCACCTTGGGCACGGGAGAGCGCCACCCGCCCGCCCCCGCCCTCGCTCCGGGTGC
```

```
GTGACCGGCCCGCCACCTTGTACAGAACCAGCACTCCCAGGGCCCGAGCGCGTGCCTTCCCGTGCGGCC

CGTGCGCAGCCGCGCTCTGCCCCTCCGTCCCCAGGGTGCAGGCGCGCACCGCCCAACCCCCACCTCCCGG

TGTATGCAGTGGTGATGCCTAAAGGAATGTCACGCA
```

In another embodiment, the NR1-2 is encoded by a nucleotide sequence having the sequence:

```
                                                               (SEQ ID NO: 5)
GTCGCCGCAGCGTCCGGACCGGAACCAGCGCCGTCCGCGGAGCCGCCGCCGCCGCCGCCGGGCCCTTTCC

AAGCCGGGCGCTCGGAGCTGTGCCCGGCCCCGCTTCAGCACCGCGGACAGCGCCGGCCGCGTGGGGCTGA

GCCCCGAGCCCCGCGCACGCTTCAGCGCCCCTTCCCTCGGCCGACGTCCCGGGACCGCCGCTCCGGGGG

AGACGTGGCGTCCGCAGCCCGCGGGGCCGGGCGAGCGCAGGACGGCCCGGAAGCCCCGCGGGGGATGCGC

CGAGGGCCCCGCGTTCGCGCCGCGCAGAGCCAGGCCCGCGGCCCGAGCCCATGAGCACCATGCGCCTGCT

GACGCTCGCCCTGCTGTTCTCCTGCTCCGTCGCCCGTGCCGCGTGCGACCCCAAGATCGTCAACATTGGC

GCGGTGCTGAGCACGCGGAAGCACGAGCAGATGTTCCGCGAGGCCGTGAACCAGGCCAACAAGCGGCACG

GCTCCTGGAAGATTCAGCTCAATGCCACCTCCGTCACGCACAAGCCCAACGCCATCCAGATGGCTCTGTC

GGTGTGCGAGGACCTCATCTCCAGCCAGGTCTACGCCATCCTAGTTAGCCATCCACCTACCCCCAACGAC

CACTTCACTCCCACCCCTGTCTCCTACACAGCCGGCTTCTACCGCATACCCGTGCTGGGGCTGACCACCC

GCATGTCCATCTACTCGGACAAGAGCATCCACCTGAGCTTCCTGCGCACCGTGCCGCCCTACTCCCACCA

GTCCAGCGTGTGGTTTGAGATGATGCGTGTCTACAGCTGGAACCACATCATCCTGCTGGTCAGCGACGAC

CACGAGGGCCGGGCGGCTCAGAAACGCCTGGAGACGCTGCTGGAGGAGCGTGAGTCCAAGGCAGAGAAGG

TGCTGCAGTTTGACCCAGGGACCAAGAACGTGACGGCCCTGCTGATGGAGGCGAAAGAGCTGGAGGCCCG

GGTCATCATCCTTTCTGCCAGCGAGGACGATGCTGCCACTGTATACCGCGCAGCCGCGATGCTGAACATG

ACGGGCTCCGGGTACGTGTGGCTGGTCGGCGAGCGCGAGATCTCGGGGAACGCCCTGCGCTACGCCCCAG

ACGGCATCCTCGGGCTGCAGCTCATCAACGGCAAGAACGAGTCGGCCCACATCAGCGACGCCGTGGGCGT

GGTGGCCCAGGCCGTGCACGAGCTCCTCGAGAAGGAGAACATCACCGACCCGCCGCGGGGCTGCGTGGGC

AACACCAACATCTGGAAGACCGGGCCGCTCTTCAAGAGAGTGCTGATGTCTTCCAAGTATGCGGATGGGG

TGACTGGTCGCGTGGAGTTCAATGAGGATGGGGACCGGAAGTTCGCCAACTACAGCATCATGAACCTGCA

GAACCGCAAGCTGGTGCAAGTGGGCATCTACAATGGCACCCACGTCATCCCTAATGACAGGAAGATCATC

TGGCCAGGCGGAGAGACAGAGAAGCCTCGAGGGTACCAGATGTCCACCAGACTGAAGATTGTGACGATCC

ACCAGGAGCCCTTCGTGTACGTCAAGCCCACGCTGAGTGATGGGACATGCAAGGAGGAGTTCACAGTCAA

CGGCGACCCAGTCAAGAAGGTGATCTGCACCGGGCCCAACGACACGTCGCCGGGCAGCCCCCGCCACACG

GTGCCTCAGTGTTGCTACGGCTTTTGCATCGACCTGCTCATCAAGCTGGCACGGACCATGAACTTCACCT

ACGAGGTGCACCTGGTGGCAGATGGCAAGTTCGGCACACAGGAGCGGGTGAACAACAGCAACAAGAAGGA

GTGGAATGGGATGATGGGCGAGCTGCTCAGCGGGCAGGCAGACATGATCGTGGCGCCGCTAACCATAAAC

AACGAGCGCGCAGTACATCGAGTTTTCCAAGCCCTTCAAGTACCAGGGCCTGACTATTCTGGTCAAGA

AGGAGATTCCCCGGAGCACGCTGGACTCGTTCATGCAGCCGTTCCAGAGCACACTGTGGCTGCTGGTGGG

GCTGTCGGTGCACGTGGTGGCCGTGATGCTGTACCTGCTGGACCGCTTCAGCCCCTTCGGCCGGTTCAAG

GTGAACAGCGAGGAGGAGGAGGAGGACGCACTGACCCTGTCCTCGGCCATGTGGTTCTCCTGGGGCGTCC

TGCTCAACTCCGGCATCGGGGAAGGCGCCCCCAGAAGCTTCTCAGCGCGCATCCTGGGCATGGTGTGGGC

CGGCTTTGCCATGATCATCGTGGCCTCCTACACCGCCAACCTGGCGGCCTTCCTGGTGCTGGACCGGCCG

GAGGAGCGCATCACGGGCATCAACGACCCTCGGCTGAGGAACCCCTCGGACAAGTTTATCTACGCCACGG
```

-continued

```
TGAAGCAGAGCTCCGTGGATATCTACTTCCGGCGCCAGGTGGAGCTGAGCACCATGTACCGGCATATGGA
GAAGCACAACTACGAGAGTGCGGCGGAGGCCATCCAGGCCGTGAGAGACAACAAGCTGCATGCCTTCATC
TGGGACTCGGCGGTGCTGGAGTTCGAGGCCTCGCAGAAGTGCGACCTGGTGACGACTGGAGAGCTGTTTT
TCCGCTCGGGCTTCGGCATAGGCATGCGCAAAGACAGCCCCTGGAAGCAGAACGTCTCCCTGTCCATCCT
CAAGTCCCACGAGAATGGCTTCATGGAAGACCTGGACAAGACGTGGGTTCGGTATCAGGAATGTGACTCG
CGCAGCAACGCCCCTGCGACCCTTACTTTTGAGAACATGGCCGGGGTCTTCATGCTGGTAGCTGGGGGCA
TCGTGGCCGGGATCTTCCTGATTTTCATCGAGATTGCCTACAAGCGGCACAAGGATGCTCGCCGGAAGCA
GATGCAGCTGGCCTTTGCCGCCGTTAACGTGTGGCGGAAGAACCTGCAGAGCACCGGGGGTGGACGCGGC
GCTTTGCAAAACCAAAAAGACACAGTGCTGCCGCGACGCGCTATTGAGAGGGAGGAGGGCCAGCTGCAGC
TGTGTTCCCGTCATAGGGAGAGCTGAGACTCCCCGCCCGCCCTCCTCTGCCCCCTCCCCCGCAGACAGAC
AGACAGACGGACGGGACAGCGGCCCGGCCCACGCAGAGCCCCGGAGCACCACGGGGTCGGGGAGGAGCA
CCCCCAGCCTCCCCCAGGCTGCGCCTGCCCGCCCGCCGGTTGGCCGGCTGGCCGGTCCACCCCGTCCCGG
CCCCGCGCGTGCCCCCAGCGTGGGGCTAACGGGCGCCTTGTCTGTGTATTTCTATTTTGCAGCAGTACCA
TCCCACTGATATCACGGGCCCGCTCAACCTCTCAGATCCCTCGGTCAGCACCGTGGTGTGAGGCCCCCGG
AGGCGCCCACCTGCCCAGTTAGCCCGGCCAAGGACACTGATGGGTCCTGCTGCTCGGGAAGGCCTGAGGG
AAGCCCACCCGCCCCAGAGACTGCCCACCCTGGGCCTCCCGTCCGTCCGCCCGCCCACCCCGCTGCCTGG
CGGGCAGCCCCTGCTGGACCAAGGTGCGGACCGGAGCGGCTGAGGACGGGGCAGAGCTGAGTCGGCTGGG
CAGGGCCGCAGGGCGCTCCGGCAGAGGCAGGGCCCTGGGGTCTCTGAGCAGTGGGGAGCGGGGCTAACT
GGCCCCAGGCGGAGGGGCTTGGAGCAGAGACGGCAGCCCCATCCTTCCCGCAGCACCAGCCTGAGCCACA
GTGGGGCCCATGGCCCCAGCTGGCTGGGTCGCCCCTCCTCGGGCGCCTGCGCTCCTCTGCAGCCTGAGCT
CCACCCTCCCCTCTTCTTGCGGCACCGCCCACCCACACCCCGTCTGCCCCTTGACCCCACACGCCGGGGC
TGGCCCTGCCCTCCCCCACGGCCGTCCCTGACTTCCCAGCTGGCAGCGCCTCCCGCCGCCTCGGGCCGCC
TCCTCCAGACTCGAGAGGGCTGAGCCCCTCCTCTCCTCGTCCGGCCTGCAGCCCAGAACGGGCCTCCCCG
GGGGTCCCCGGACGCTGGCTCGGGACTGTCTTCAACCCTGCCCTGCACCTTGGGCACGGGAGAGCGCCAC
CCGCCCGCCCCCGCCCTCGCTCCGGGTGCGTGACCGGCCCGCCACCTTGTACAGAACCAGCACTCCCAGG
GCCCGAGCGCGTGCCTTCCCCGTGCGGCCCGTGCGCAGCCGCGCTCTGCCCCTCCGTCCCCAGGGTGCAG
GCGCGCACCGCCCAACCCCCACCTCCCGGTGTATGCAGTGGTGATGCCTAAAGGAATGTCACGCA
```

In another embodiment, the NR1-1 is encoded by a nucleotide sequence having the sequence:

(SEQ ID NO: 6)
```
GTCGCCGCAGCGTCCGGACCGGAACCAGCGCCGTCCGCGGAGCCGCCGCCGCCGCCGGGCCCTTTCC
AAGCCGGGCGCTCGGAGCTGTGCCCGGCCCCGCTTCAGCACCGCGGACAGCGCCGGCCGCGTGGGGCTGA
GCCCCGAGCCCCGCGCACGCTTCAGCGCCCCTTCCCTCGGCCGACGTCCCGGGACCGCCGCTCCGGGGG
AGACGTGGCGTCCGCAGCCCGCGGGGCCGGGCGAGCGCAGGACGGCCGGAAGCCCCGCGGGGATGCGC
CGAGGGCCCCGCGTTCGCGCCGCGCAGAGCCAGGCCCGCGGCCCGAGCCCATGAGCACCATGCGCCTGCT
GACGCTCGCCCTGCTGTTCTCCTGCTCCGTCGCCCGTGCCGCGTGCGACCCCAAGATCGTCAACATTGGC
GCGGTGCTGAGCACGCGGAAGCACGAGCAGATGTTCCGCGAGGCCGTGAACCAGGCCAACAAGCGGCACG
GCTCCTGGAAGATTCAGCTCAATGCCACCTCCGTCACGCACAAGCCCAACGCCATCCAGATGGCTCTGTC
GGTGTGCGAGGACCTCATCTCCAGCCAGGTCTACGCCATCCTAGTTAGCCATCCACCTACCCCCAACGAC
CACTTCACTCCCACCCCTGTCTCCTACACAGCCGGCTTCTACCGCATACCCGTGCTGGGGCTGACCACCC
```

-continued

```
GCATGTCCATCTACTCGGACAAGAGCATCCACCTGAGCTTCCTGCGCACCGTGCCGCCCTACTCCCACCA
GTCCAGCGTGTGGTTTGAGATGATGCGTGTCTACAGCTGGAACCACATCATCCTGCTGGTCAGCGACGAC
CACGAGGGCCGGGCGGCTCAGAAACGCCTGGAGACGCTGCTGGAGGAGCGTGAGTCCAAGGCAGAGAAGG
TGCTGCAGTTTGACCCAGGGACCAAGAACGTGACGGCCCTGCTGATGGAGGCGAAAGAGCTGGAGGCCCG
GGTCATCATCCTTTCTGCCAGCGAGGACGATGCTGCCACTGTATACCGCGCAGCCGCGATGCTGAACATG
ACGGGCTCCGGGTACGTGTGGCTGGTCGGCGAGCGCGAGATCTCGGGGAACGCCCTGCGCTACGCCCCAG
ACGGCATCCTCGGGCTGCAGCTCATCAACGGCAAGAACGAGTCGGCCCACATCAGCGACGCCGTGGGCGT
GGTGGCCCAGGCCGTGCACGAGCTCCTCGAGAAGGAGAACATCACCGACCCGCCGCGGGGCTGCGTGGGC
AACACCAACATCTGGAAGACCGGGCCGCTCTTCAAGAGAGTGCTGATGTCTTCCAAGTATGCGGATGGGG
TGACTGGTCGCGTGGAGTTCAATGAGGATGGGGACCGGAAGTTCGCCAACTACAGCATCATGAACCTGCA
GAACCGCAAGCTGGTGCAAGTGGGCATCTACAATGGCACCCACGTCATCCCTAATGACAGGAAGATCATC
TGGCCAGGCGGAGAGACAGAGAAGCCTCGAGGGTACCAGATGTCCACCAGACTGAAGATTGTGACGATCC
ACCAGGAGCCCTTCGTGTACGTCAAGCCCACGCTGAGTGATGGGACATGCAAGGAGGAGTTCACAGTCAA
CGGCGACCCAGTCAAGAAGGTGATCTGCACCGGGCCCAACGACACGTCGCCGGGCAGCCCCCGCCACACG
GTGCCTCAGTGTTGCTACGGCTTTTGCATCGACCTGCTCATCAAGCTGGCACGGACCATGAACTTCACCT
ACGAGGTGCACCTGGTGGCAGATGGCAAGTTCGGCACACAGGAGCGGGTGAACAACAGCAACAAGAAGGA
GTGGAATGGGATGATGGGCGAGCTGCTCAGCGGGCAGGCAGACATGATCGTGGCGCCGCTAACCATAAAC
AACGAGCGCGCGCAGTACATCGAGTTTTCCAAGCCCTTCAAGTACCAGGGCCTGACTATTCTGGTCAAGA
AGGAGATTCCCCGGAGCACGCTGGACTCGTTCATGCAGCCGTTCCAGAGCACACTGTGGCTGCTGGTGGG
GCTGTCGGTGCACGTGGTGGCCGTGATGCTGTACCTGCTGGACCGCTTCAGCCCCTTCGGCCGGTTCAAG
GTGAACAGCGAGGAGGAGGAGGAGGACGCACTGACCCTGTCCTCGGCCATGTGGTTCTCCTGGGGCGTCC
TGCTCAACTCCGGCATCGGGGAAGGCGCCCCCAGAAGCTTCTCAGCGCGCATCCTGGGCATGGTGTGGGC
CGGCTTTGCCATGATCATCGTGGCCTCCTACACCGCCAACCTGGCGGCCTTCCTGGTGCTGGACCGGCCG
GAGGAGCGCATCACGGGCATCAACGACCCTCGGCTGAGGAACCCCTCGGACAAGTTTATCTACGCCACGG
TGAAGCAGAGCTCCGTGGATATCTACTTCCGGCGCCAGGTGGAGCTGAGCACCATGTACCGGCATATGGA
GAAGCACAACTACGAGAGTGCGGCGGAGGCCATCCAGGCCGTGAGAGACAACAAGCTGCATGCCTTCATC
TGGGACTCGGCGGTGCTGGAGTTCGAGGCCTCGCAGAAGTGCGACCTGGTGACGACTGGAGAGCTGTTTT
TCCGCTCGGGCTTCGGCATAGGCATGCGCAAAGACAGCCCCTGGAAGCAGAACGTCTCCCTGTCCATCCT
CAAGTCCCACGAGAATGGCTTCATGGAAGACCTGGACAAGACGTGGGTTCGGTATCAGGAATGTGACTCG
CGCAGCAACGCCCCTGCGACCCTTACTTTTGAGAACATGGCCGGGGTCTTCATGCTGGTAGCTGGGGGCA
TCGTGGCCGGGATCTTCCTGATTTTCATCGAGATTGCCTACAAGCGGCACAAGGATGCTCGCCGGAAGCA
GATGCAGCTGGCCTTTGCCGCCGTTAACGTGTGGCGGAAGAACCTGCAGCAGTACCATCCCACTGATATC
ACGGGCCCGCTCAACCTCTCAGATCCCTCGGTCAGCACCGTGGTGTGAGGCCCCGGAGGCGCCCACCTG
CCCAGTTAGCCCGGCCAAGGACACTGATGGGTCCTGCTGCTCGGGAAGGCCTGAGGGAAGCCCACCCGCC
CCAGAGACTGCCCACCCTGGGCCTCCCGTCCGTCCGCCCGCCCACCCCGCTGCCTGGCGGGCAGCCCCTG
CTGGACCAAGGTGCGGACCGGAGCGGCTGAGGACGGGGCAGAGCTGAGTCGGCTGGGCAGGGCCGCAGGG
CGCTCCGGCAGAGGCAGGGCCCTGGGGTCTCTGAGCAGTGGGGAGCGGGGGCTAACTGGCCCCAGGCGGA
GGGGCTTGGAGCAGAGACGGCAGCCCCATCCTTCCCGCAGCACCAGCCTGAGCCACAGTGGGGCCCATGG
CCCCAGCTGGCTGGGTCGCCCCTCCTCGGGCGCCTGCGCTCCTCTGCAGCCTGAGCTCCACCCTCCCCTC
TTCTTGCGGCACCGCCCACCCACACCCCGTCTGCCCCTTGACCCCACACGCCGGGGCTGGCCCTGCCCTC
CCCCACGGCCGTCCCTGACTTCCCAGCTGGCAGCGCCTCCCGCCGCCTCGGGCCGCCTCCTCCAGACTCG
```

-continued

```
AGAGGGCTGAGCCCCTCCTCTCCTCGTCCGGCCTGCAGCCCAGAACGGGCCTCCCCGGGGGTCCCCGGAC

GCTGGCTCGGGACTGTCTTCAACCCTGCCCTGCACCTTGGGCACGGGAGAGCGCCACCCGCCCGCCCCCG

CCCTCGCTCCGGGTGCGTGACCGGCCCGCCACCTTGTACAGAACCAGCACTCCCAGGGCCCGAGCGCGTG

CCTTCCCCGTGCGGCCCGTGCGCAGCCGCGCTCTGCCCCTCCGTCCCCAGGGTGCAGGCGCGCACCGCCC

AACCCCCACCTCCCGGTGTATGCAGTGGTGATGCCTAAAGGAATGTCACGCA
```

In another embodiment, the NR1 subunit is encoded by a nucleotide molecule that is a homologue of SEQ ID NOs: 4, 5, or 6. In another embodiment, the nucleotide molecule is a variant of SEQ ID NOs: 4, 5, or 6. In another embodiment, the nucleotide molecule is an isomer of SEQ ID NOs: 4, 5, or 6. In another embodiment, the nucleotide molecule is a fragment of SEQ ID NOs: 4, 5, or 6. In another embodiment, the nucleotide molecule comprises SEQ ID NOs: 4, 5, or 6. Each possibility represents a separate embodiment of the present invention.

The epitope recognized by an antibody detected by a method of the present invention is, in another embodiment, a conformational epitope. In another embodiment, the epitope is a linear epitope. In another embodiment, the epitope is any other type of epitope known in the art. Each possibility represents a separate embodiment of the present invention. In one embodiment, antibody to an NR1 subunit of an NMDA receptor binds to extra cellular N-terminal domain of said NR1 subunit. In another embodiment, the antibody binds to a region comprising amino acids 25-380 of SEQ ID NO: 1. In another embodiment, the antibody binds to a region comprising a functional fragment of amino acids 25-380 of SEQ ID NO: 1.

The discovery of NR1-related antibodies in the serum and CSF of all patients provides in one embodiment, a diagnostic test for the paraneoplastic anti-NMDAR encephalitis disorder, and provides a novel immune-mediated mechanism of NMDAR dysfunction. In one embodiment, critical roles of NMDARs include synaptic transmission and remodeling, or dendritic sprouting, and hippocampal long-term potentiation in other embodiments in addition to one paradigm of memory formation and learning. In another embodiment, NMDARs are also the major mediator of excitotoxicity, and their dysfunction has been associated with schizophrenia, epilepsy, and several types of dementia. Drugs interacting with NMDARs may result in paranoia in one embodiment, or hallucinations and dyskinesias in certain embodiments, all frequent symptoms in subjects diagnosed using the methods described herein.

In one embodiment, ectopic expression of NR1 subunit by nervous tissue contained in the teratomas contributes to break immune tolerance. In another embodiment, a combination of factors such as an adjuvant effect of the prodromal viral-like illness that occur in most subjects, and a genetic predisposition in certain embodiments, play additional roles in the initiation of the immune response tested for using the diagnosis methods described herein.

In one embodiment, a pathogenic role of NR1 antibodies in paraneoplastic anti-NMDAR encephalitis is shown by the correlation between patients' symptoms and antibody titers.

In another embodiment, the subject has exhibits antibodies that react with SIZN1 (Smad-Interacting Zinc finger protein expressed in the Nervous system).

In another embodiment, the subject has exhibits antibodies that react with a VGKC antigen.

In another embodiment, the subject exhibits antibodies that react with an extracellular neuronal antigen. In another embodiment, the subject exhibits antibodies that react with an antigen exposed on the cell surface of a neuron. In another embodiment, patients with antibodies to extracellular antigens exhibit, under the conditions utilized herein, enhanced responsiveness to immune therapy.

In another embodiment, a method of the present invention utilizes, detects, or tests for a target antigen (other than a NR1 subunit) identified by a method disclosed herein. In another embodiment, the target antigen is identified by a library screening technique. In another embodiment, the target antigen is identified by cDNA library screening. In another embodiment, the target antigen is identified by reactivity with cultured neurons. Each possibility represents a separate embodiment of the present invention.

In another embodiment, the present invention provides a method of diagnosing encephalitis in a subject, comprising the steps of obtaining a biological sample from the subject; and testing the biological sample for an antibody to an NR multimer of an NMDA receptor, whereby said NR multimer comprises an NR1 subunit, and whereby a presence of said antibody in said biological sample indicates an autoimmune encephalitis, thereby determining a cause of an encephalitis in a subject.

In another embodiment, the present invention provides a method of diagnosing a tumor associated with an autoimmune encephalitis in a subject, comprising the steps of: obtaining a biological sample from the subject; and testing the biological sample for an antibody to an NR multimer of an NMDA receptor, whereby said NR multimer comprises an NR1 subunit, and whereby a presence of said antibody indicates a presence of an occult tumor in said subject and that said tumor is a cause of said autoimmune encephalitis.

In another embodiment, the present invention provides a method of diagnosing epilepsy in a subject, comprising the steps of: obtaining a biological sample from the subject; and testing the biological sample for the presence of an antibody to an NR multimer of an NMDA receptor, whereby said NR multimer comprises an NR1 subunit, and whereby a presence of said antibody indicates a presence of a tumor in said subject and said tumor is a cause of said epilepsy, thereby diagnosing epilepsy in a subject.

In another embodiment, the present invention provides a method of diagnosing a tumor in a subject having an epilepsy, comprising the step of: obtaining a biological sample from the subject; and testing the biological sample for the presence of an antibody to an NR multimer of an NMDA receptor, whereby said NR multimer comprises an NR1 subunit, and whereby a presence of said antibody indicates a presence of a tumor in said subject, thereby diagnosing a tumor in a subject having an epilepsy.

In another embodiment, the present invention provides a method of treating autoimmune encephalitis in a subject, comprising the steps of: detecting a tumor associated with an autoimmune encephalitis by testing a body fluid from the subject for an antibody to an NR multimer of an NMDA receptor, whereby said NR multimer comprises an NR1 subunit, whereby a presence of said antibody indicates a presence of said tumor in said subject and that said tumor is a cause of said autoimmune encephalitis; and treating said tumor. In another embodiment, the tumor is treated within four months of the onset of a symptom associated with autoimmune encephalitis.

Methods for testing a reactivity of a body fluid against neuronal antigens are well known in the art. In one embodiment, enzyme-linked immunoabsorption assay (ELISA) is used to test for the presence of an antibody. In another embodiment, immunocytochemistry is used to test for the presence of an antibody. In another embodiment, immunoprecipitation is used to test for the presence of an antibody. In another embodiment, one of the methods enumerated herein is utilized. In another embodiment, neuronal tissue is fixed with PFA. In another embodiment, any other method known in the art is utilized. Each possibility represents a separate embodiment of the present invention.

In another embodiment, the present invention provides a kit comprising a compound or composition utilized in performing a method of the present invention. In another embodiment, the present invention provides a kit comprising a composition, tool, or instrument of the present invention. Each possibility represents a separate embodiment of the present invention.

Methods and kits for detection of antibodies are well known in the art, and are described, for example, in Ances B M et al (Treatment-responsive limbic encephalitis identified by neuropil antibodies: MRI and PET correlates. Brain 2005; 128:1764-1777) and Vitaliani et al (Paraneoplastic encephalitis, psychiatric symptoms, and hypoventilation in ovarian teratoma. Ann Neurol 2005; 58:594-604.). Each possibility represents a separate embodiment of the present invention.

Methods for diagnosing limbic encephalitis (LE) are well known in the art. In another embodiment, patients with LE develop subacute confusion, irritability, depression, sleep disturbances, seizures, short-term memory loss, and/or dementia. In another embodiment, the pathological substrate of LE is an inflammatory disorder that predominantly involves the limbic system (hippocampi, amygdala, and cingulate gyrus). In another embodiment, biopsy and autopsy studies demonstrate interstitial and perivascular infiltrates of T cells, and less frequently B cells, along with microglial activation, neuronal degeneration, and/or gliosis. In another embodiment, inflammatory infiltrates are found in areas distant from the limbic system. In another embodiment, the infiltrates remain mild and clinically silent. In another embodiment, the infiltrates become prominent and develop into a disorder called encephalomyelitis. Additional methods of diagnosing LE are described, for example, in Gultekin S H et al (Paraneoplastic limbic encephalitis: neurological symptoms, immunological findings and tumour association in 50 patients. Brain 2000; 123:1481-1494). Each possibility represents a separate embodiment of the present invention.

In another embodiment, an antigen of the present invention is homologous to a peptide disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-2 of greater than 70%. In another embodiment, "homology" refers to identity to a sequence selected from SEQ ID No: 1-2 of greater than 72%. In another embodiment, "homology" refers to identity to one of SEQ ID No: 1-2 of greater than 75%. In another embodiment, "homology" refers to identity to a sequence selected from SEQ ID No: 1-2 of greater than 78%. In another embodiment, "homology" refers to identity to one of SEQ ID No: 1-2 of greater than 80%. In another embodiment, "homology" refers to identity to one of SEQ ID No: 1-2 of greater than 82%. In another embodiment, "homology" refers to identity to a sequence selected from SEQ ID No: 1-2 of greater than 83%. In another embodiment, "homology" refers to identity to one of SEQ ID No: 1-2 of greater than 85%. In another embodiment, "homology" refers to identity to one of SEQ ID No: 1-2 of greater than 87%. In another embodiment, "homology" refers to identity to a sequence selected from SEQ ID No: 1-2 of greater than 88%.

In another embodiment, "homology" refers to identity to one of SEQ ID No: 1-2 of greater than 90%. In another embodiment, "homology" refers to identity to one of SEQ ID No: 1-2 of greater than 92%. In another embodiment, "homology" refers to identity to a sequence selected from SEQ ID No: 1-2 of greater than 93%. In another embodiment, "homology" refers to identity to one of SEQ ID No: 1-2 of greater than 95%. In another embodiment, "homology" refers to identity to a sequence selected from SEQ ID No: 1-2 of greater than 96%. In another embodiment, "homology" refers to identity to one of SEQ ID No: 1-2 of greater than 97%. In another embodiment, "homology" refers to identity to one of SEQ ID No: 1-2 of greater than 98%. In another embodiment, "homology" refers to identity to one of SEQ ID No: 1-2 of greater than 99%. In another embodiment, "homology" refers to identity to one of SEQ ID No: 1-2 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

EXAMPLES

Materials and Methods

Clinical and immunological criteria. Clinical information was obtained by the inventors of the instant application or provided by referring physicians, and has been partially reported on 21 patients. All patients had brain MRI, serological or CSF studies that ruled out other disorders, and screening for a systemic neoplasm. Serum and CSF were tested for antibodies to NMDA receptor, and considered positive if three criteria were fulfilled as shown in FIG. 1. Antibody titers were measured by enzyme-linked immunoabsorption assay (Elisa) on HEK293 cell lysates expressing NR1 or NR1/NR2B heteromers. Studies were approved by the University of Pennsylvania Institutional Review Board.

Neurological outcome was assessed using the Modified Rankin Scale (MRS) and Minimental State Examination (MMSE). Patients were considered to have "full recovery" when they returned to their jobs (MRS 0, MMSE 29-30); "mild deficits", when they returned to most activities of daily living and remained stable for at least two months (MRS 1-2; MMSE>25-28), and "severe deficits" for all other cases.

Figure 6:
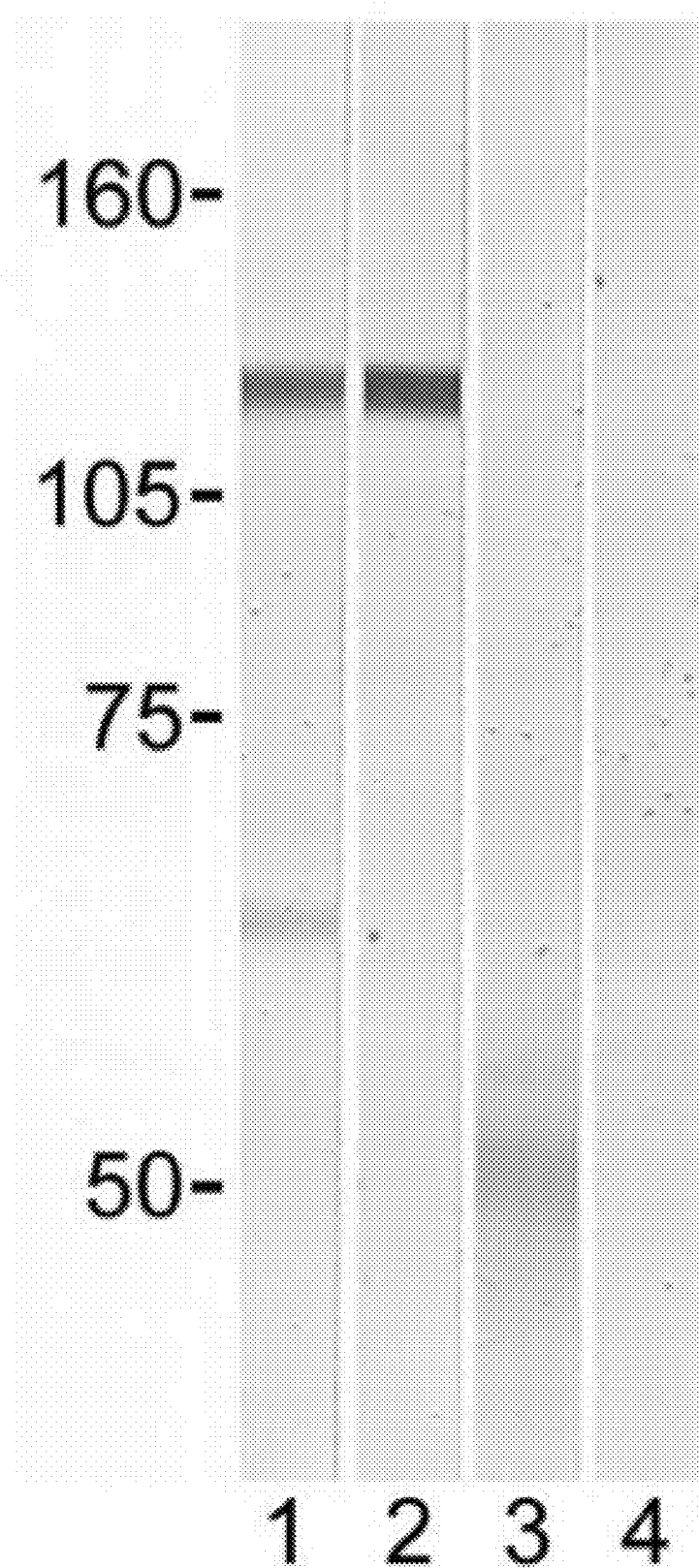
FIG. 6: Co-precipitation of assembled NR1d4 and NR2B subunits. The assembly of NR1d4 with NR2B is demonstrated by the co-precipitation of NR1d4 from a metal chromatography column that binds to the His tag of NR2B. The immunoblot strips containing the eluate from the column were incubated with an antibody to NR2B (lane 1), V5 (lane 2), NR1 (lane 3), and secondary antibodies only (lane 4). The isolated NR2B (~120 kDa) is visible with both the antibody specifically directed against NR2B (lane 1) and the antibody against V5 (lane 2). In lane 1, the band at ~62 kDa is a proteolytic fragment. The co-precipitated NR1d4 is demonstrated in lane 3 (~50 kDa).

Analysis of subunit targets and epitope region. HEK293 cells transfected with rodent (or human) NR1, or NR2 (A, B, C or D), or co-transfected with NR1 and NR2 plasmids in equimolar ratios were fixed in 4% paraformaldehyde, permeabilized with 0.3% Triton X-100 and incubated with patients' sera (diluted 1:200) or CSF (1:10). To confirm that the reactivity of patients' antibodies occurred with cells expressing the indicated subunits, all studies were performed with double immunolabeling using a rabbit monoclonal antibody to NR1 (1:10,000, Chemicon, Temecula, Calif.) or rabbit polyclonal antibodies to NR2A (1:200, Upstate, Lake Placid, N.Y.), NR2B (1:200, Zymed, San Francisco, Calif.), and NR2C (1:200, Chemicon). Subsequently, cells were washed and incubated with the appropriate Alexa fluor secondary antibodies for 1 hour at room temperature. Results were photographed under a fluorescence microscope using Zeiss Axiovision software. To determine the location of the main epitope region, we took advantage of the property of NR1 to stably assemble by itself, and of a modified NR1 subunit (NR1d4) in which amino acids 25-380 are deleted, and still assembles with NR2B (FIG. 6). The reactivity of patients' antibodies with these heteromers (NR1d4/NR2B) was examined by immunocytochemistry as above.

Patients and Controls. Clinical information and test results were obtained by the inventors of the instant application or provided by referring physicians and patients' family members. Overall, 133 patients were identified since the initial report of this disorder in 12 patients. The current study includes the first 100 patients for whom clinical information and adequate follow-up are available. In all cases serum, CSF, and tissue (when available) were kept frozen at −80° C., until study. Sera or CSF of 250 individuals were used as controls. They included 50 patients with classical limbic encephalitis (25 paraneoplastic, 25 idiopathic), 25 with limbic encephalitis or Morvan's syndrome associated with voltage-gated potassium channel (VGKC) antibodies, 50 with other paraneoplastic disorders, 20 with Rasmussen's encephalitis, 25 with chronic epilepsy of unknown etiology, 10 viral encephalitis, 50 cancer patients without neurological symptoms (10 had teratomas of the ovary), and 20 blood donors. Overall, 210 sera and 180 CSF samples from these individuals were examined using the techniques and criteria shown in FIG. 1. None of the samples fulfilled criteria #1 and #3. Samples from 32 patients with classical limbic encephalitis had other antibodies reacting with the cell surface of neurons (criteria #2, unknown antigen); none of these patients had ovarian teratoma. Overall, applying the three criteria of FIG. 1, none of the 250 subjects had anti-NMDA receptor antibodies.

Analysis of assembly of NR1d4/NR2B using immunoprecipitation and immunoblot. To determine if NR1d4 (with amino acids 25-380 deleted) assembles with NR2, HEK293 cells were transfected with NR1d4 and a modified NR2B construct. The modified NR2B has the intracellular C-terminus (which does not contribute to immunoreactivity) replaced by a short sequence encoding a 6-His tag motif and a viral epitope (V5) tag (pcDNA3.1/V5-HisTopo vector). After transfection, cells were harvested and solubilized in RIPA buffer, a condition that extracts NMDA receptors but does not disrupt the NR1 and NR2B complex. The NR1d4/NR2B complexes were then purified by metal chromatography and eluted with imidazole. Eluted complexes were then separated in a 8% polyacrylamide gel electrophoresis, transferred to nitrocellulose and incubated with a rabbit polyclonal antibody against NR1 (1:1000, AB9864, Chemicon, Temecula, Calif.), NR2B (1:200, Zymed, San Francisco, Calif.), or mouse monoclonal antibody against V5 (1:1000, Invitrogen, San Diego, Calif.). Results from this study are shown in FIG. 6.

Enzyme-linked immunoabsorption assay (Elisa). Having demonstrated that the main epitope region in NR1/NR2 heteromers resides in NR1, an Elisa was developed to quantify the levels of antibodies. For these studies, HEK293 cells transfected with plasmids containing NR1 (or NR1 and NR2B) were lysed with 1% Triton X-100, 150 mM NaCl, 1 mM EDTA, 100 mM Tris-HCl, 0.5% deoxycholate acid containing protease inhibitor cocktail (diluted 1:50, P8340, Sigma, Saint Louis, Mo.), centrifugated at 7000×g for 10 minutes, and the supernatant (containing the NR1 or NR1/NR2B subunits) isolated and proteins measured.

Figure 3:
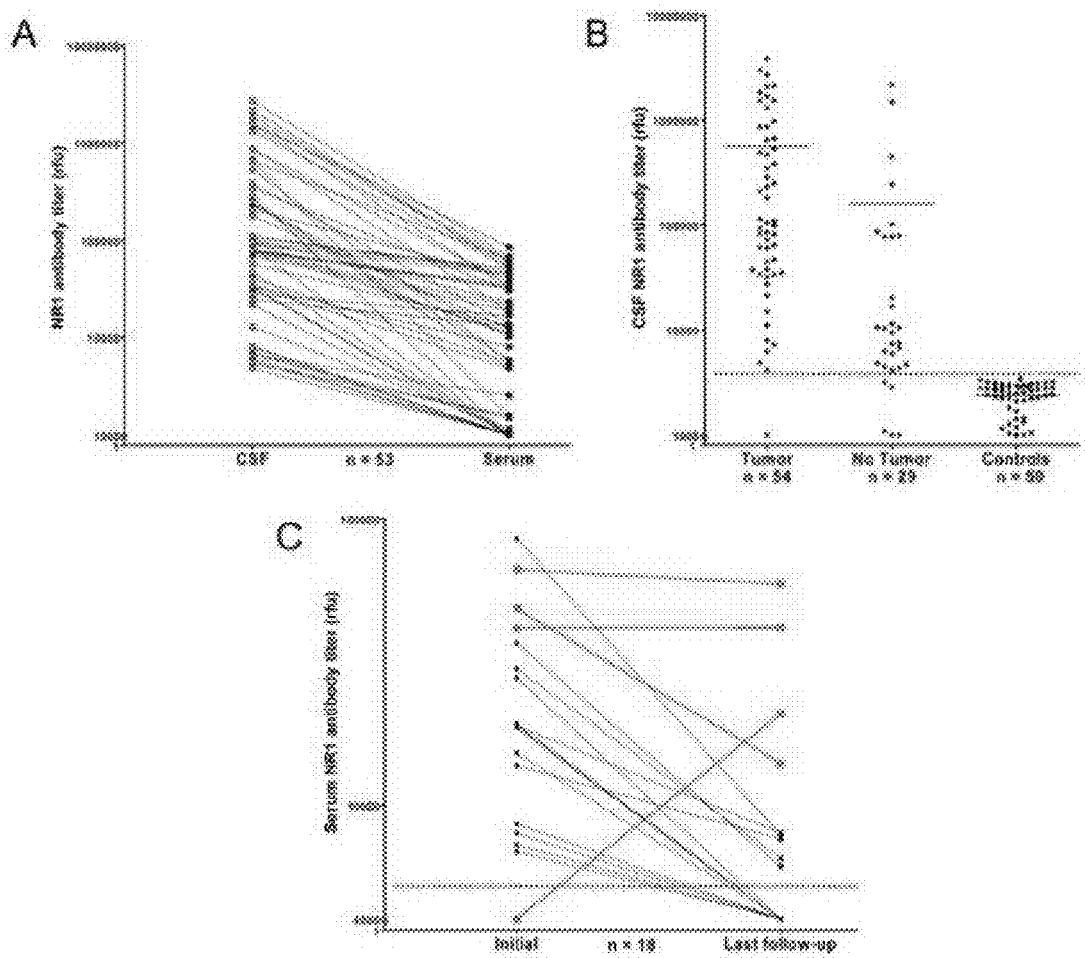
FIG. 3: Analysis of NR1 antibody titers. (A) Comparison of NR1 antibody titers using the same amount of IgG from paired CSF and serum of 53 patients with anti-NMDA receptor encephalitis. In all cases antibody titers were higher in CSF than serum. (B) CSF antibody titers in 83 patients with anti-NMDA receptor encephalitis (54 with tumor, 29 without tumor) and 50 controls. Solid lines indicate the mean of the titers in each group. Dotted line indicates 3 standard deviations above the mean value given by background signal of negative controls. Patients with a tumor had higher titers than those without tumor (Wilcoxon rank, p<0.01) and controls (p<0.01). 6 patients (1 with tumor, 5 without tumor) had very low Elisa readings that overlapped with the signal given by negative controls. These 6 patients had low antibody titers by the criteria of FIG. 1; in contrast, applying the same criteria the 50 controls were negative. (C) Follow-up of serum antibody titers in 14 representative patients who had neurological improvement (black lines) and 4 who did not improve (red lines). The second time point corresponds to the sample obtained at the last follow-up (2-83 months, median 5.6). Dotted line indicates 3 standard deviations of the mean value given by background signal of 50 negative control sera. Similar results were obtained using Elisa with NR1/NR2 heteromers. Values in A, B and C are given in relative fluorescence units (rfu) from the Elisa reader, and plotted in a logarithmic scale.

Ninety-six well Elisa plates (Costar, Corning, N.Y.) were then coated with rabbit NR1 antibody (Chemicon) diluted 1:500 in carbonate-bicarbonate buffer pH 9.6 overnight at 4° C., blocked with 5% goat serum diluted in PBS for 1 hour, and then incubated with the indicated supernatant (8 mg/ml) containing the NR1 (or NR1/NR2B) subunits for 1 hour at 37° C. Wells with captured NR1 subunits were then washed with 0.05% Tween-20 in PBS, and incubated with patients' serum or CSF for 1 hour at 37° C. Paired serum and CSF were used after normalizing the amount of total IgG; all samples were used at dilutions in the linear range of Elisa readings. Plates were washed with 0.05% Tween-20 in PBS, incubated with the appropriate secondary anti-human IgG (1:2000, Jackson Immunologicals, West Grove, Pa.) for 1 hour at 37° C., washed with 0.05% Tween-20 in PBS, incubated with Amplex Ultrared (Invitrogen, Eugene, Oreg.) for 30 minutes in the dark and the reactivity measured in an Elisa reader (Biotech, Windoski, Vt.). Elisa wells coated and treated as above except for the use of cell lysates (8 mg/ml) of non-transfected HEK293 (or HEK293 cells transfected with a control plasmid) were used to determine the non-specific (or background) reactivity of patients' samples. The specific reactivity of patients' samples with NR1 was obtained by subtracting the readings of plates without NR1 from the readings of plates with captured NR1. All patients' samples were measured in triplicate. A monoclonal mouse antibody to NR1 (1:200, BD Biosciences, San Diego, Calif.) and the appropriate secondary antibody was used as a control and to normalize readings among plates. Fifty serum and 50 CSF samples without NR1/NR2 antibodies were randomly selected from the indicated control samples and used as controls for the Elisa studies. Results of these studies are shown in FIG. 3.

Figure 4:
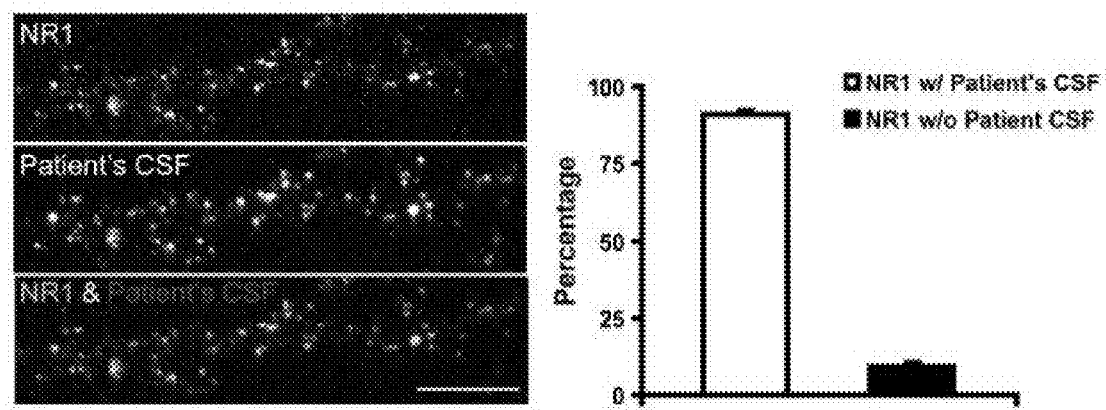
FIG. 4: Immunolabeling of neuronal NR1 clusters. 14 div hippocampal neurons immunostained for NR1 (b+w, green) or patient's CSF (b+w, red). Scale bar=10 μm. Right: Nearly all NR1 clusters are co-labeled with patient's CSF (91%, yellow puncta in overlay), less than 9% of NR1-positive puncta remain unlabeled (seen as green in overlay). Kruskal-Wallis non-parametric ANOVA followed by Dunn's pairwise comparison, p<0.01.

Quantitative analysis of NMDA receptor clusters using confocal microscopy. Embryonic rat hippocampal neurons were cultured. To determine the degree of immunolabeling of NMDA receptors by patients' antibodies, 14 div rat hippocampal neurons were incubated with patient's CSF (1:15 dilution in Triton X-100) and a rabbit polyclonal antibody against NR1 (1:1000, Chemicon) for 2 hours followed by the appropriate fluorescent conjugated secondary antibody (Jackson Immunologicals). Images were obtained using a laser-scanning confocal microscope (Leica TCS SP2). For each image, laser light levels and detector gain and offset were adjusted so that no pixel values were saturated. Images were thresholded, and the number of individual clusters along neuronal dendrites was determined using interactive software (Meta-Morph; Universal Imaging, West Chester, Pa.). Results of these studies are shown in FIG. 4.

Figure 5:
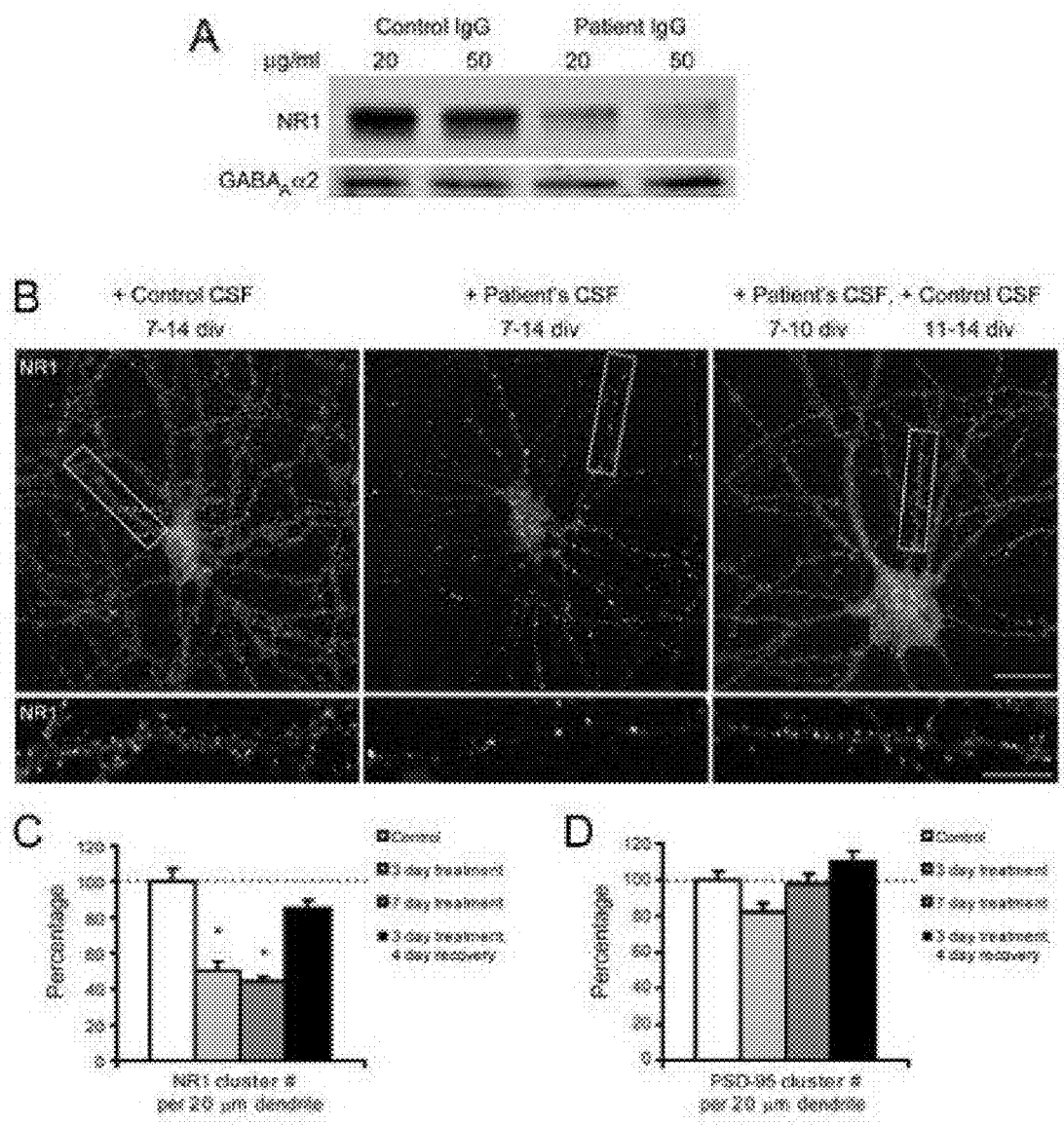
FIG. 5: Patient's antibodies specifically and reversibly reduce the number of NMDA receptor clusters in live neurons. (A) Representative immunoblot of neuronal surface NR1 levels after application of control or patient IgG (llg/ml). Protein concentrations were normalized to levels of $GABA_A$ receptor subunit α2. (B) Hippocampal neurons cultured with control CSF or patient CSF from 7-10 div (7 day treatment), or with patient CSF from 7-10 div followed by control CSF from 11-14 div (3 day treatment and 4 day recovery), then immunostained for NR1 (N=18-36 cells from each of 3 experiments). Scale bar=25 μm. Boxed areas are shown below at higher magnification. Scale bar=10 μm. (C) Patient CSF applied for 3 or 7 days significantly reduced the number of NR1 labeled clusters compared to cultures treated with control CSF or cultures treated with patient CSF followed by 4 day recovery. (N=18-36 cells from each of 3 experiments; Kruskal-Wallis non-parametric ANOVA, Dunn's pairwise comparison, p<0.01). (D) Application of patient CSF for 3 or 7 days did not significantly affect the number of PSD-95 clusters (N=18-36 cells from each of 3 experiments; p>0.05).

To determine the effects of patients' antibodies on the number of NMDA receptor clusters, neurons were treated with patient or control CSF (1:15 dilution in NeuroBasal+ B27 medium, GIBCO, Carlsbad, Calif.) daily from 7 to 14 div. Each day, 20 of the 300 µl of medium in each culture well was removed and replaced with 20 µl of fresh patient or control CSF. In another series of experiments, neurons were treated with patient CSF from 7 to 10 div followed by treatment with control CSF from 10 to 14 div. On 10 or 14 div, neurons were fixed in freshly made paraformaldehyde (4% paraformaldehyde, 4% sucrose in PBS) for 5 minutes, permeablized in 0.25% Triton X-100 for 10 minutes, and blocked in 5% normal goat serum for 1 hour. Neurons were then incubated with patient's CSF (1:15 dilution in Triton X-100), a rabbit polyclonal antibody against NR1 (1:1000, Chemicon) or a mouse monoclonal antibody against PSD-95 (1:500, Affinity BioReagents, Golden, Colo.) for 2 hours followed by the appropriate fluorescent-conjugated secondary antibodies (Jackson Immunologicals). Images were obtained using a laser-scanning confocal microscope and analyzed as above. Results of these studies are shown in FIG. 5B-D.

Quantitative analysis of NMDA receptors using immunoblot of cell surface biotinylated proteins. Surface biotinylations were performed in 15 to 21 div rat hippocampal neurons isolated from E18 embryos. IgG was isolated from serum on a mixed protein A/protein G column and eluted in 0.1M Na-citrate buffer, pH 2.7. Neurons were treated for 24 hours with purified IgG from control individuals or patients, washed twice in cold PBS with 1 mM MgCl2 and 0.1 mM CaCl2 (buffer A, pH 7.35), and incubated shaking for 30 minutes at 4° C. in buffer A plus 1 mg/ml EZ Link Sulfo-NHS-Biotin (Pierce, Rockford, Ill.). Excess biotin was then quenched by washing for 20-30 minutes at 4° C. with buffer A supplemented with 100 mM glycine. Cells were then washed twice in buffer A and incubated shaking in lysis buffer (150 mM NaCl, 1 mM EDTA, 100 mM Tris HCl, 1% Triton X-100, 1% sodium deoxycholate, 0.1% SDS, pH 7.4) for 1 hour at 4° C. Cells were collected and cleared by 20 minute centrifugation at 13,000×g. An aliquot of lysate was saved as the lysate fraction; this fraction was also used to measure protein concentration. A second aliquot was added to Immobilized Monomeric Avidin beads (Pierce) and incubated for 1 hour at room temperature or overnight at 4° C. Samples were then centrifuged for 15 minutes at 13,000×g and the supernatant was saved as the intracellular fraction. The beads were then washed once in lysis buffer, twice in high-salt buffer (500 mM NaCl, 50 mM Tris, 5 mM EDTA, 0.1% Triton X-100, pH 7.5), and once in no-salt buffer (50 mM Tris, pH 7.5). The surface fraction was eluted by incubation with SDS sample buffer (120 mM Tris, 1% bromophenol blue, 20% glycerol, 2% mercaptoethanol) at 37° C. for 30 minutes. All fractions were then analyzed by immunoblot. Briefly, equal amounts of protein were loaded onto 8% SDS-polyacrylamide gels and transferred to nitrocellulose membranes. Membranes were blocked with 3% non-fat milk and incubated with primary antibody for 2 hours at room temperature or overnight at 4° C. The antibodies used included, anti-NR1 (BD Pharmingen 556308, diluted 1:1000) and anti-GABA$_A$ α2 (Chemicon AB5948, diluted 1:1000). Blots were then incubated with horseradish peroxidase-conjugated secondary antibody and visualized using enhanced chemiluminescence (Pierce). Protein levels were quantified by scanning densitometry using NIH Image 1.62. GABA$_A$ receptor subunit a2 was used as a loading control against which NR1 levels were normalized. To ensure that the surface fraction reflected only surface proteins, blots were also probed for actin; actin levels in the surface fraction were consistently below 15% of the level in the cell lysate. Results of these studies are shown in FIG. 5A.

Quantitative immunoblot analysis of cell surface NMDA receptors. Cultures of embryonic rat hippocampal neurons were incubated for 24 hours with IgG isolated from patients or control serum. Subsequently the cell surface proteins were biotinylated and isolated from the whole cell lysate. The NR1 surface levels from neurons treated with patients' or control IgG were then quantified using immunoblot analysis.

Statistics. Statistical analyses were conducted using SAS 9.1 (SAS Institute, Cary, N.C.). Contingency tables were analyzed using Fisher's two-sided exact test. Differences in antibody titers among groups were analyzed using the Kruskal-Wallis and Wilcoxon sum rank tests, with the Bonferroni correction for pair-wise tests. The effects of IgG and CSF on neuronal cultures were analyzed using the Kruskal-Wallis non-parametric ANOVA followed by Dunn's pairwise comparison.

Example 1

Neurological Syndrome

Clinical information is shown in Table 1. Eighty-six percent of patients had headache, low-grade fever, or a non-specific viral-like illness within two weeks before hospital admission. Seventy-seven patients presented with prominent psychiatric symptoms, including anxiety, agitation, bizarre behavior, delusional or paranoid thoughts, and visual or auditory hallucinations. Twenty-three patients presented with short-term memory loss or seizures alone or associated with psychiatric manifestations. During the first three weeks of symptom presentation 76 patients had seizures. Subsequently 88 patients developed decreased level of consciousness, progressing to a "catatonic-like state", with periods of akinesis alternating with agitation, and diminished or paradoxical responses to stimuli (e.g., no response to pain but resisting eye opening). Some patients mumbled unintelligible words or had echolalia. Eye contact or visual tracking was absent or inconsistent. During this stage 86 patients developed dyskinesias, 69 autonomic instability, and 66 central hypoventilation (median time of ventilatory support, 8 weeks; range 2-40 weeks). The most characteristic dyskinesias were orofacial (55%) including grimacing, masticatory-like movements, and forceful jaw opening and closing, resulting in lip and tongue injuries or broken teeth. Thirty-seven patients had cardiac dysrhythmias, including tachycardia or bradycardia, with prolonged pauses in 7 patients; 4 required a pacemaker. Dyskinesias, autonomic instability, and hypoventilation overlapped in 52 patients; two of these problems occurred in 27 patients, and one in 14. The remaining 7 cases developed a milder syndrome, including seizures and psychiatric symptoms.

TABLE 1

Clinical Features and Treatment

| Characteristic | Subjects |
|---|---|
| Female sex - no. (%) | 91 (91) |
| Age - yr, range (median) | |
| Range | 5-76 |
| Median | 23 |
| Prodromal symptoms in 84 assessable cases - no. (%) | 72 (86) |
| Symptom presentation - no. (%) | |
| Psychiatric (initially seen by psychiatrist) | 77 (77) |
| Neuro-psychiatric (initially seen by neurologists) | 23 (23) |
| Seizures - no. (%) | |
| Any type | 76 (76) |
| Generalized tonic-clonic | 45 (45) |
| Partial complex | 10 (10) |
| Other[a] | 30 (30) |
| Dyskinesias and movement disorders - no. (%) | |
| Any type | 86 (86) |
| Orofacial | 55 (55) |
| Choreoathetoid and complex movements with extremities, abdomen or pelvis | 47 (47) |
| Abnormal postures (dystonic, extension), muscle rigidity, or increased tone | 47 (47) |
| Other[b] | 25 (25) |
| Autonomic instability(c) - no. (%) | 69 (69) |
| Central hypoventilation - no. (%) | 66 (66) |
| EEG in 92 assessable cases - no. (%) | |
| Total with abnormal findings | 92 (100) |
| Slow activity[d] | 71 (77) |
| Epileptic activity | 21 (23) |
| Brain MRI- no. (%) | |
| Total with abnormal findings | 55 (55) |
| Medial temporal lobes | 22 (22) |
| Cerebral cortex | 17 (17) |
| Cerebellum | 6 (6) |
| Brainstem | 6 (6) |
| Basal ganglia | 5 (5) |
| Contrast enhancement in cortex, meninges, basal ganglia | 14 (14) |
| Other(e) | 8 (8) |
| CSF - no. (%) | |
| Total with abnormal findings | 95 (95) |
| Lymphocytic pleocytosis | 91 (91) |
| Range, cells/lil | 5-480 |
| Median | 32 |
| Increased protein concentration | 32 (32) |
| Range, mg/dl | 49-213 |
| Median | 67 |
| Oligoclonal bands in 39 assessable cases | 26 (67) |
| Tumor in 98 assessable patients - no. (%) | 58 (59) |
| Women | |
| Mature teratoma of the ovary | 35 (36) |
| Inmature teratoma of the ovary | 14 (14) |
| Radiologically demonstrated teratoma | 4 (4) |
| Other(f) | 3 (3) |
| Men | |
| Immature teratoma of the testis | 1 (1) |
| Small-cell lung cancer | 1 (1) |
| Treatment - no. (%) | |
| Tumor resection | 51 (51) |
| Immunotherapy | 94 (94) |
| Corticosteroids | 76 (76) |
| IVIG | 62 (62) |
| Plasma exchange | 34 (34) |
| Rituximab | 10 (10) |
| Cyclophosphamide | 9 (9) |
| Azathioprine | 1 (1) |
| Other[g] | 10 (10) |
| Only supportive care | 2 (2) |

[a]8 secondary generalized seizures, 6 refractory status epilepticus, 7 focal motor, 7 not classified, 2 epilepsia partialis continua.
[b]9 myoclonus, 8 abnormal ocular movements (eye deviation, nystagmus or ocular dipping), 5 tremor, 3 balismus.
[c]37 cardiac dysrhythmia (16 tachycardia, 7 bradycardia, 14 both); 36 dysthermia (27 hyperthermia, 3 hypothermia, 6 both); 21 blood pressure instability (12 hypertension, 3 hypotension, 6 both); 20 hyperhydrosis; 18 sialorrhea; 6 hyperpnea; 4 adynamic ileus.
[d]EEG delta or theta activity, generalized or in frontotemporal regions.
[e]Other areas of abnormal signal in MRI FLAIR/T2: 4 corpus callosum, 2 hypothalamus, 1 periventricular, 1 multifocal white matter change.
[f]1 sex-cord stromal tumor, 1 neuroendrocine tumor, 1 teratoma of the mediastinum.
[g]7 chemotherapy, 3 electroconvulsive therapy.

EEG, brain MRI, and CSF findings are shown in Table 1. Most patients had extensive EEG monitoring that in 77% of cases revealed generalized or predominantly fronto-temporal slow or disorganized activity (delta-theta) without epileptic discharges. Fifty five patients had abnormal fluid-attenuated inversion recovery (FLAIR) or T2 MRI findings; 14 patients had faint or transient contrast enhancement of the cerebral cortex, overlaying meninges, or basal ganglia. Fourteen patients underwent brain biopsy, 2 were normal, 12 showed mild perivascular lymphocytic cuffing and 10 microglial activation. All were negative for neuronophagic nodules and viral studies.

Example 2

Tumor Association

Fifty-eight of 98 patients (59%) had a neoplasm (Table 1); two died before tumor evaluation. All but one of these patients developed neurological symptoms before the tumor diagnosis (median 8 weeks, range 1-380 weeks). In 6 patients, the tumor was diagnosed after recovery from the encephalitis (56-380 months). In 53 patients, the tumor was a teratoma of the ovary (median size 6 cm, range 1-22), identified with CT, MRI, or ultrasound. Eight patients had bilateral teratomas; 4 were synchronous, 2 had history of a contralateral teratoma, and 2 developed contralateral teratomas heralding recurrence of the encephalitis. All teratomas contained nervous tissue; 25 were examined for expression of NMDA receptors, and all were positive.

One boy (11 years old, without tumor) and 21 women were younger than 19 years (median 15, range 5-18); 12 had an ovarian teratoma (5 immature) and 9 had no tumor. Metastases were identified only in one man with immature teratoma of the testis.

Example 3

Treatment and Outcome

Figure 2:
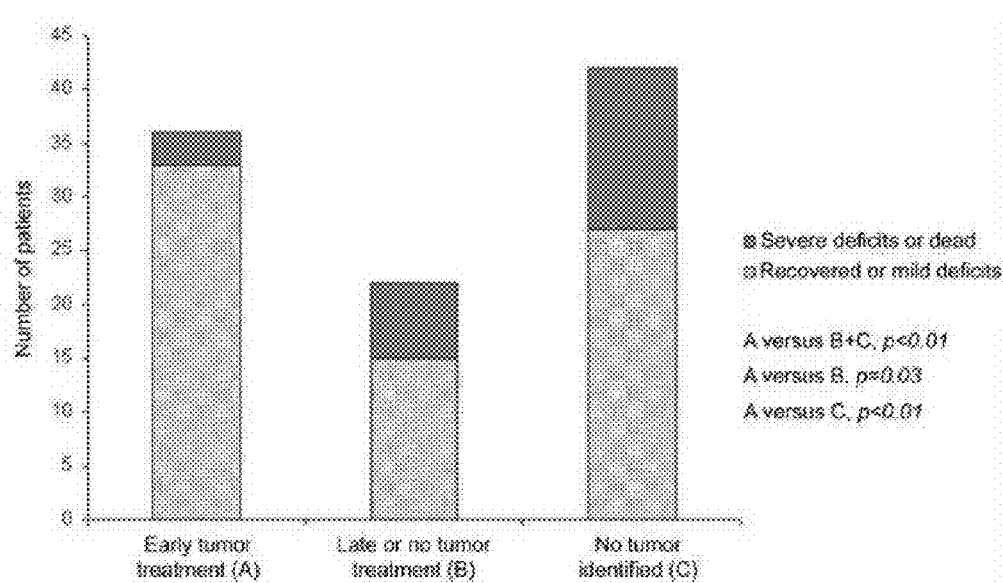
FIG. 2: Response to treatment. Patients who had the tumor diagnosed and treated within 4 months of neurological symptom development had better outcomes (full recovery or mild deficits) than the rest of the patients (p<0.01), including patients whose tumor was treated after 4 months of neurological symptom development or not treated (p=0.03), and patients without tumor (p<0.01). See Table 2 for more details.

Fifty-one patients had tumor resection and 7 did not (1 small-cell lung cancer, 2 teratomas found at autopsy, 4 not removed). All but 6 patients who had tumor removal received one or more immunotherapies (Table 1). Similar immunotherapies were used in 40 of 42 patients without tumor and 2 had supportive care. The median follow-up was 17 months (1-194): 47 patients had full recovery, 28 mild stable deficits, 18 severe deficits, and 7 died as a result of the neurological disorder. Patients whose tumor was identified and removed within the first 4 months of the onset of the neurological disease had better outcome than the rest of the patients ($p<0.01$; FIG. 2, and Table S1). The median time from symptom presentation to initial signs of improvement was 8 weeks (range 2-24) for the group of patients with early tumor treatment, 11 weeks (4-40) for the group whose tumor was treated late or not treated, and 10 weeks (2-50) for the group without tumor (Kruskal-Wallis, $p=0.10$).

The median duration of hospitalization was 2.5 months (range 1-14). While hospitalized, 7 patients had high levels of serum creatine kinase, 6 developed pulmonary embolism, 6 transient aphasia, 4 hemiparesis and 4 tetraparesis. After discharge, 85% of the patients who were left with mild deficits or eventually attained full recovery had signs of frontal lobe dysfunction including poor attention and planning, impulsivity, and behavioral dysinhibition; 26% had prominent sleep dysfunction, including hypersomnia and inversion of sleep patterns.

Relapses of encephalitis were less frequent in patients with early tumor treatment (1 of 36) than the rest of the patients (14 of 64; $p<0.01$) including patients whose tumor was treated late or not treated (6 of 22; $p<0.01$), and patients without tumor (8 of 42; $p=0.03$).

Seven patients died of the neurological disorder. In all 7 cases the diagnosis was established retrospectively by examining archived CSF.

Example 4

Antibodies Target the Amino-Terminal Extracellular Domain of NR1

Analysis of the reactivity of patients' sera or CSF with the indicated NMDA receptor subunits or heteromers showed that the antibody reactivity was not modified by changing the NR2 subunit (A, B, C, or D) and was retained by homomers of NR1 (Table 3). Having established that NR1 was recognized by all patients' antibodies, the epitope region was examined using an NR1 plasmid (NR1d4) that codes for a subunit deleted at amino acids 25-380 and is able to assemble with NR2B. The successful expression of NR1d4/NR2B in HEK293 cells was confirmed by immunocytochemistry using the indicated mouse and rabbit antibodies to NR1 and NR2B. The use of these heteromers abrogated the reactivity of 92 patients' serum or CSF samples, and substantially decreased the reactivity of the samples of the remaining 8 cases. These results indicate that the main epitope region recognized by all patients' antibodies resides in amino acids 25-380 of NR1 (Table 3).

TABLE 2

| | Neurological Outcome | | | |
|---|---|---|---|---|
| | Total (=100) | Early tumor treatment[a] (=36) | Late or no tumor treatment[b] (=22) | No tumor detected[c] (=42) |
| Full recovery | 47 | 26 | 8 | 13 |
| Mild deficits | 28 | 7 | 7 | 14 |
| Severe deficits | 18 | 2 | 4 | 12 |
| Dead | 7 | 1 | 3 | 3 |

[a]Patients whose tumor was treated within 4 months of developing neurological symptoms, usually in association with immunotherapy.
[b]Patients whose tumor was treated after 4 months of developing neurological symptoms or only received immunotherapy.
[c]Patients without tumor detected after a follow-up of 5-79 months (median 15) The group of patients with early tumor treatment had better outcome (full recovery, mild deficits) than the rest of the patients (Fisher's exact test, p < 0.01), including patients whose tumor was treated late or not treated (p = 0.03) and patients without tumor p < 0.01).

TABLE 3

Analysis of reactivity of patients' antibodies with NR subunits and heteromers

| Subunits or heteromers | Total patients examined | Total positive |
|---|---|---|
| NR1/NR2B | 100 | 100 |
| NR1/NR1 | 100 | 100 |
| *NR1d4/NR2B | 100 | 8 |
| NR1/NR2A | 50 | 50 |
| NR1/NR2C | 50 | 50 |
| NR1/NR2D | 25 | 25 |
| NR2A | 50 | 6 |
| NR2B | 75 | 8 |
| NR2C | 50 | 4 |

*NR1d4: construct in which amino acids 25-380 were deleted

Example 5

Elisa Antibody Titers in Serum and CSF

In order to determine whether patients had intrathecal synthesis of antibodies, the integrity of the blood-brain barrier was first measured. Of 58 patients with paired serum and CSF available, 53 had preserved integrity of the blood-brain barrier. Using normalized concentrations of IgG from CSF and serum, all 53 patients had higher antibody titers in CSF, indicating intrathecal synthesis of antibodies (FIG. 3A). Considering all patients whose CSF was available (=83), those with a tumor had higher titers than those without tumor (Wilcoxon rank, p<0.01) and controls (p<0.01, FIG. 3B). Four patients who died and whose CSF was available were among the group with the highest titers, while the 7 patients with milder syndromes had the lowest titers. Patients who improved had a parallel decrease of serum titers while those who did not improve maintained high titers in CSF and serum (FIG. 3C). Follow-up CSF titers were not obtained in most patients during or after improvement.

Example 6

Antibodies Decrease NMDA Receptor Clusters in Postsynaptic Dendrites

To assess the effect of patients' antibodies on neuronal cultures, the extent of immunolabeling of NR1 (or NMDA receptor) clusters in postsynaptic dendrites was determined. FIG. 4 shows that 91% of NMDA clusters were labeled by patients' antibodies. This antibody binding did not cause apoptosis. However, application of patients' IgG into rat hippocampal neuronal cultures produced a concentration-dependent decrease of the cell surface levels of NMDA receptors (FIG. 5A). IgG from patients with high antibody titers produced a greater decrease of NMDA receptors than IgG from patients with low antibody titers.

The effect of patients' antibodies on NMDA receptor clusters in postsynaptic dendrites was quantified by confocal microscopy. This study showed that neurons treated with patients' CSF for 3 or 7 days had significantly fewer NMDA receptor clusters per length of postsynaptic dendrite than neurons treated with control CSF. In contrast, neurons treated for 3 days with patients' CSF followed by 4 days with control CSF showed a number of NMDA receptor clusters similar to that of neurons treated only with control CSF (FIGS. 5B and C). Patients' antibodies did not modify the levels of the postsynaptic protein PSD-95 (FIG. 5D). Together, these findings demonstrate that patients' antibodies produce a selective and reversible decrease of NMDA receptor clusters in postsynaptic dendrites.

Example 7

Autopsy Studies and Neuropathological Findings

Seven patients died as a result of the neurological disorder, and in all the diagnosis was established retrospectively by examining CSF kept frozen from the time of symptom presentation. Two patients had been diagnosed with a tumor before death; one had a small-cell lung cancer with systemic metastases and the other an immature teratoma of the ovary that had been successfully removed. In two patients an unsuspected ovarian teratoma was found at autopsy (1.5 cm and 3.5 cm mature teratomas).

Overall 5 autopsies were performed; 3 included examination of the brain and 1 the brain and spinal cord. Results have been reported in 3 patients. In the 4 subjects studied there were mild to moderate inflammatory infiltrates, prominent microglial proliferation and gliosis, and minimal neuronal degeneration. Microglial nodules and neuronophagia were rarely seen. In all cases these findings predominated in the hippocampus, but also affected other areas of the brain, brainstem and spinal cord. In two patients the brain was examined for deposits of IgG and complement; both cases showed IgG that predominated in the hippocampus, without complement.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

SEQUENCE LISTING

<160> NUMBER OF SEQ ID NOS: 6

<210> SEQ ID NO 1
<211> LENGTH: 938
<212> TYPE: PRT
<213> ORGANISM: Homo sapiens

<400> SEQUENCE: 1

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95
```

```
Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp His Glu Gly Arg Ala Ala
                165                 170                 175

Gln Lys Arg Leu Glu Thr Leu Leu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525
```

```
Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Ala Val Met
                565                 570                 575

Leu Tyr Leu Leu Asp Arg Phe Ser Pro Phe Gly Arg Phe Lys Val Asn
                580                 585                 590

Ser Glu Glu Glu Glu Asp Ala Leu Thr Leu Ser Ser Ala Met Trp
                595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
                675                 680                 685

Val Asp Ile Tyr Phe Arg Arg Gln Val Glu Leu Ser Thr Met Tyr Arg
                690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
    755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
    835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Gly Arg Gly Ala Leu Gln Asn Gln
                900                 905                 910

Lys Asp Thr Val Leu Pro Arg Arg Ala Ile Glu Arg Glu Glu Gly Gln
                915                 920                 925

Leu Gln Leu Cys Ser Arg His Arg Glu Ser
    930                 935
```

```
<210> SEQ ID NO 2
<211> LENGTH: 938
<212> TYPE: PRT
<213> ORGANISM: Homo sapiens

<400> SEQUENCE: 2

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
                35                  40                  45

Ala Asn Lys Arg His Gly Ser Trp Lys Ile Gln Leu Asn Ala Thr Ser
            50                  55                  60

Val Thr His Lys Pro Asn Ala Ile Gln Met Ala Leu Ser Val Cys Glu
65              70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
        210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
                260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
        290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
                340                 345                 350

Ile Met Asn Leu Gln Asn Arg Lys Leu Val Gln Val Gly Ile Tyr Asn
            355                 360                 365

Gly Thr His Val Ile Pro Asn Asp Arg Lys Ile Ile Trp Pro Gly Gly
        370                 375                 380

Glu Thr Glu Lys Pro Arg Gly Tyr Gln Met Ser Thr Arg Leu Lys Ile
```

```
                385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
                420                 425                 430
Lys Val Ile Cys Thr Gly Pro Asn Asp Thr Ser Pro Gly Ser Pro Arg
                435                 440                 445
His Thr Val Pro Gln Cys Cys Tyr Gly Phe Cys Ile Asp Leu Leu Ile
                450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
                500                 505                 510
Ile Val Ala Pro Leu Thr Ile Asn Asn Glu Arg Ala Gln Tyr Ile Glu
                515                 520                 525
Phe Ser Lys Pro Phe Lys Tyr Gln Gly Leu Thr Ile Leu Val Lys Lys
                530                 535                 540
Glu Ile Pro Arg Ser Thr Leu Asp Ser Phe Met Gln Pro Phe Gln Ser
545                 550                 555                 560
Thr Leu Trp Leu Leu Val Gly Leu Ser Val His Val Val Ala Val Met
                565                 570                 575
Leu Tyr Leu Leu Asp Arg Phe Ser Pro Phe Gly Arg Phe Lys Val Asn
                580                 585                 590
Ser Glu Glu Glu Glu Glu Asp Ala Leu Thr Leu Ser Ser Ala Met Trp
                595                 600                 605
Phe Ser Trp Gly Val Leu Leu Asn Ser Gly Ile Gly Glu Gly Ala Pro
                610                 615                 620
Arg Ser Phe Ser Ala Arg Ile Leu Gly Met Val Trp Ala Gly Phe Ala
625                 630                 635                 640
Met Ile Ile Val Ala Ser Tyr Thr Ala Asn Leu Ala Ala Phe Leu Val
                645                 650                 655
Leu Asp Arg Pro Glu Glu Arg Ile Thr Gly Ile Asn Asp Pro Arg Leu
                660                 665                 670
Arg Asn Pro Ser Asp Lys Phe Ile Tyr Ala Thr Val Lys Gln Ser Ser
                675                 680                 685
Val Asp Ile Tyr Phe Arg Arg Gln Val Glu Leu Ser Thr Met Tyr Arg
                690                 695                 700
His Met Glu Lys His Asn Tyr Glu Ser Ala Ala Glu Ala Ile Gln Ala
705                 710                 715                 720
Val Arg Asp Asn Lys Leu His Ala Phe Ile Trp Asp Ser Ala Val Leu
                725                 730                 735
Glu Phe Glu Ala Ser Gln Lys Cys Asp Leu Val Thr Thr Gly Glu Leu
                740                 745                 750
Phe Phe Arg Ser Gly Phe Gly Ile Gly Met Arg Lys Asp Ser Pro Trp
                755                 760                 765
Lys Gln Asn Val Ser Leu Ser Ile Leu Lys Ser His Glu Asn Gly Phe
                770                 775                 780
Met Glu Asp Leu Asp Lys Thr Trp Val Arg Tyr Gln Glu Cys Asp Ser
785                 790                 795                 800
Arg Ser Asn Ala Pro Ala Thr Leu Thr Phe Glu Asn Met Ala Gly Val
                805                 810                 815
```

```
Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
        850                 855                 860

Arg Lys Ser Gly Arg Ala Glu Pro Asp Pro Lys Lys Ala Thr Phe
865                 870                 875                 880

Arg Ala Ile Thr Ser Thr Leu Ala Ser Ser Phe Lys Arg Arg Ser
                885                 890                 895

Ser Lys Asp Thr Ser Thr Gly Gly Arg Gly Ala Leu Gln Asn Gln
                900                 905                 910

Lys Asp Thr Val Leu Pro Arg Arg Ala Ile Glu Arg Glu Gly Gln
            915                 920                 925

Leu Gln Leu Cys Ser Arg His Arg Glu Ser
            930                 935

<210> SEQ ID NO 3
<211> LENGTH: 885
<212> TYPE: PRT
<213> ORGANISM: Homo sapiens

<400> SEQUENCE: 3

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255
```

-continued

```
Asn Ala Leu Arg Tyr Ala Pro Asp Gly Ile Leu Gly Leu Gln Leu Ile
                260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
        290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685
```

```
Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Gln
    850                 855                 860

Tyr His Pro Thr Asp Ile Thr Gly Pro Leu Asn Leu Ser Asp Pro Ser
865                 870                 875                 880

Val Ser Thr Val Val
                885

<210> SEQ ID NO 4
<211> LENGTH: 4376
<212> TYPE: DNA
<213> ORGANISM: Homo sapiens

<400> SEQUENCE: 4
gtcgccgcag cgtccggacc ggaaccagcg ccgtccgcgg agccgccgcc gccgccgccg      60
ggccctttcc aagccgggcg ctcggagctg tgccggccc cgcttcagca ccgcggacag     120
cgccggccgc gtgggctga gccccgagcc ccgcgcacg cttcagcgcc ccttccctcg      180
gccgacgtcc cgggaccgcc gctcggggg agacgtggcg tccgcagccc gcggggccgg     240
gcgagcgcag gacggcccgg aagccccgcg ggggatgcgc cgagggcccc gcgttcgcgc     300
cgcgcagagc caggcccgcg gcccgagccc atgagcacca tgcgcctgct gacgctcgcc     360
ctgctgttct cctgctccgt cgcccgtgcc ggtgcgacc caagatcgt caacattggc     420 gcggtgctga gcacgcggaa gcacgagcag atgttccgcg aggccgtgaa ccaggccaac     480
aagcggcacg gctcctggaa gattcagctc aatgccacct ccgtcacgca caagcccaac     540
gccatccaga tggctctgtc ggtgtgcgag gacctcatct ccagccaggt ctacgccatc     600
ctagttagcc atccacctac ccccaacgac cacttcactc ccacccctgt ctcctacaca     660
gccggcttct accgcatacc cgtgctgggg ctgaccaccc gcatgtccat ctactcggac     720
aagagcatcc acctgagctt cctgcgcacc gtgccgccct actcccacca gtccagcgtg     780
tggtttgaga tgatgcgtgt ctacagctgg aaccacatca tcctgctggt cagcgacgac     840
cacgagggcc gggcggctca gaaacgcctg gagacgctgc tggaggagcg tgagtccaag     900
gcagagaagg tgctgcagtt tgacccaggg accaagaacg tgacggccct gctgatggag     960
```

```
gcgaaagagc tggaggcccg ggtcatcatc ctttctgcca gcgaggacga tgctgccact   1020
gtataccgcg cagccgcgat gctgaacatg acgggctccg ggtacgtgtg gctggtcggc   1080
gagcgcgaga tctcggggaa cgccctgcgc tacgccccag acggcatcct cgggctgcag   1140
ctcatcaacg gcaagaacga gtcggcccac atcagcgacg ccgtgggcgt ggtggcccag   1200
gccgtgcacg agctcctcga aggagaaac atcaccgacc cgccgcgggg ctgcgtgggc   1260
aacaccaaca tctggaagac cgggccgctc ttcaagagag tgctgatgtc ttccaagtat   1320
gcggatgggg tgactggtcg cgtggagttc aatgaggatg gggaccggaa gttcgccaac   1380
tacagcatca tgaacctgca gaaccgcaag ctggtgcaag tgggcatcta caatggcacc   1440
cacgtcatcc ctaatgacag gaagatcatc tggccaggcg gagagacaga gaagcctcga   1500
gggtaccaga tgtccaccag actgaagatt gtgacgatcc accaggagcc cttcgtgtac   1560
gtcaagccca cgctgagtga tgggacatgc aaggaggagt tcacagtcaa cggcgaccca   1620
gtcaagaagg tgatctgcac cgggcccaac gacacgtcgc cgggcagccc ccgccacacg   1680
gtgcctcagt gttgctacgg cttttgcatc gacctgctca tcaagctggc acggaccatg   1740
aacttcacct acgaggtgca cctggtggca gatggcaagt tcggcacaca ggagcgggtg   1800
aacaacagca acaagaagga gtggaatggg atgatgggcg agctgctcag cgggcaggca   1860
gacatgatcg tggcgccgct aaccataaac aacgagcgcg cgcagtacat cgagttttcc   1920
aagcccttca gtaccaggg cctgactatt ctggtcaaga aggagattcc ccggagcacg   1980
ctggactcgt tcatgcagcc gttccagagc acactgtggc tgctggtggg gctgtcggtg   2040
cacgtggtgg ccgtgatgct gtacctgctg gaccgcttca gccccttcgg ccggttcaag   2100
gtgaacagcg aggaggagga ggaggacgca ctgaccctgt cctcggccat gtggttctcc   2160
tggggcgtcc tgctcaactc cggcatcggg gaaggcgccc ccagaagctt ctcagcgcgc   2220
atcctgggca tggtgtgggc cggctttgcc atgatcatcg tggcctccta caccgccaac   2280
ctggcggcct tcctggtgct ggaccggccg gaggagcgca tcacgggcat caacgacccc   2340
cggctgagga acccctcgga caagtttatc tacgccacgg tgaagcagag ctccgtggat   2400
atctacttcc ggcgccaggt ggagctgagc accatgtacc ggcatatgga gaagcacaac   2460
tacgagagtg cggcggaggc catccaggcc gtgagagaca acaagctgca tgccttcatc   2520
tgggactcgg cggtgctgga gttcgaggcc tcgcagaagt gcgacctggt gacgactgga   2580
gagctgtttt tccgctcggg cttcggcata ggcatgcgca agacagccc ctggaagcag   2640 aacgtctccc tgtccatcct caagtccac gagaatggct tcatggaaga cctgacaag   2700 acgtgggttc ggtatcagga atgtgactcg cgcagcaacg cccctgcgac ccttactttt   2760
gagaacatgg ccggggtctt catgctgta gctgggggca tcgtggccgg gatcttcctg   2820
attttcatcg agattgccta caagcggcac aaggatgctc gccggaagca gatgcagctg   2880
gcctttgccg ccgttaacgt gtggcggaag aacctgcagg atagaaagag tggtagagca   2940
gagcctgacc ctaaaaagaa agccacatt agggctatca cctccacct ggcttccagc   3000 ttcaagaggc gtaggtcctc aaagacacg agcaccgggg gtggacgcgg cgcttttgcaa   3060 aaccaaaaag acacagtgct gccgcgacgc gctattgaga gggaggaggg ccagctgcag   3120
ctgtgttccc gtcatagga gagctgagac tccccgcccg ccctcctctg ccccctcccc   3180
cgcagacaga cagacagacg gacgggacag cggccggcc cacgcagagc cccggagcac   3240
cacggggtcg ggggaggagc acccccagcc tcccccaggc tgcgcctgcc cgccgccgg   3300 ttggccggct ggccggtcca ccccgtcccg gcccgcgcg tgcccccagc gtggggctaa   3360
```

```
cgggcgcctt gtctgtgtat ttctattttg cagcagtacc atcccactga tatcacgggc    3420
ccgctcaacc tctcagatcc ctcggtcagc accgtggtgt gaggccccg gaggcgccca     3480 cctgcccagt tagcccggcc aaggacactg atgggtcctg ctgctcggga aggcctgagg    3540
gaagcccacc cgcccagag actgccacc ctgggcctcc cgtccgtccg cccgcccacc      3600
ccgctgcctg gcgggcagcc cctgctggac caaggtgcgg accggagcgg ctgaggacgg    3660
ggcagagctg agtcggctgg gcagggccga agggcgctcc ggcagaggca gggccctggg   3720
gtctctgagc agtggggagc gggggctaac tggccccagg cggaggggct tggagcagag    3780
acggcagccc catccttccc gcagcaccag cctgagccac agtggggccc atggcccag    3840 ctggctgggt cgcccctcct cgggcgcctg cgctcctctg cagcctgagc tccaccctcc   3900
cctcttcttg cggcaccgcc cacccacacc cgtctgccc cttgacccca cacgccgggg   3960
ctggccctgc cctcccccac ggccgtccct gacttcccag ctggcagcgc ctcccgccgc   4020
ctcgggccgc ctcctccaga ctcgagaggg ctgagcccct cctctcctcg tccggcctgc   4080
agcccagaac gggcctcccc ggggtcccc ggacgctggc tcgggactgt cttcaaccct    4140
gccctgcacc ttgggcacgg gagagcgcca cccgcccgcc ccgcccctcg ctccgggtgc   4200
gtgaccggcc cgccaccttg tacagaacca gcactcccag ggcccgagcg cgtgccttcc   4260
ccgtgcggcc cgtgcgcagc cgcgctctgc ccctccgtcc ccagggtgca ggcgcgcacc   4320
gcccaacccc cacctcccgg tgtatgcagt ggtgatgcct aaaggaatgt cacgca       4376

<210> SEQ ID NO 5
<211> LENGTH: 4265
<212> TYPE: DNA
<213> ORGANISM: Homo sapiens

<400> SEQUENCE: 5
gtcgccgcag cgtccggacc ggaaccagcg ccgtccgcgg agccgccgcc gccgccgccg      60 ggcccttcc aagccgggcg ctcggagctg tgcccggccc cgcttcagca ccgcggacag     120
cgccggccgc gtggggctga gcccgagcc cccgcgcacg cttcagcgcc ccttccctcg     180
gccgacgtcc cggaccgcc gctccggggg agacgtggcc tccgcagccc gcggggccgg    240
gcgagcgcag gacggcccgg aagcccgcg ggggatgcgc cgagggcccc gcgttcgcgc    300
cgcgcagagc caggcccgcg gcccgagccc atgagcacca tgcgcctgct gacgctcgcc   360
ctgctgttct cctgctccgt cgcccgtgcc gcgtgcgacc ccaagatcgt caacattggc   420
gcggtgctga gcacgcggaa gcacgagcag atgttccgcg aggccgtgaa ccaggccaac   480
aagcggcacg gctcctggaa gattcagctc aatgccacct ccgtcacgca caagcccaac   540
gccatccaga tggctctgtc ggtgtgcgag gacctcatct ccagccaggt ctacgccatc   600
ctagttagcc atccacctac ccccaacgac cacttcactc ccaccctgt ctcctacaca    660 gccggcttct accgcatacc cgtgctgggg ctgaccaccc gcatgtccat ctactcggac   720
aagagcatcc acctgagctt cctgcgcacc gtgccgccct actcccacca gtccagcgtg   780
tggtttgaga tgatgcgtgt ctacagctgg aaccacatca tcctgctggt cagcgacgac   840
cacgagggcc gggcggctca gaaacgcctg agacgctgc tggaggagcg tgagtccaag   900
gcagagaagg tgctgcagtt tgacccaggg accaagaacg tgacgccct gctgatggag   960 gcgaaagagc tggaggcccg ggtcatcatc cttctctgcca gcgaggacga tgctgccact  1020
gtataccgcg cagccgcgat gctgaacatg acgggctccg ggtacgtgtg gctggtcggc   1080
gagcgcgaga tctcggggaa cgccctgcgc tacgccccag acggcatcct cggggctgcag  1140
```

```
ctcatcaacg gcaagaacga gtcggcccac atcagcgacg ccgtgggcgt ggtggcccag   1200
gccgtgcacg agctcctcga gaaggagaac atcaccgacc cgccgcgggg ctgcgtgggc   1260
aacaccaaca tctggaagac cgggccgctc ttcaagagag tgctgatgtc ttccaagtat   1320
gcggatgggg tgactggtcg cgtggagttc aatgaggatg ggaccggaa gttcgccaac    1380 tacagcatca tgaacctgca gaaccgcaag ctggtgcaag tgggcatcta caatggcacc   1440
cacgtcatcc ctaatgacag gaagatcatc tggccaggcg agagacaga gaagcctcga    1500 gggtaccaga tgtccaccag actgaagatt gtgacgatcc accaggagcc cttcgtgtac   1560
gtcaagccca cgctgagtga tgggacatgc aaggaggagt tcacagtcaa cggcgaccca   1620
gtcaagaagg tgatctgcac cgggcccaac gacacgtcgc cgggcagccc ccgccacacg   1680
gtgcctcagt gttgctacgg cttttgcatc gacctgctca tcaagctggc acggaccatg   1740
aacttcacct acgaggtgca cctggtggca gatggcaagt tcggcacaca ggagcgggtg   1800
aacaacagca caagaagga gtggaatggg atgatgggcg agctgctcag cgggcaggca    1860
gacatgatcg tggcgccgct aaccataaac aacgagcgcg cgcagtacat cgagttttcc   1920
aagcccttca gtaccagggg cctgactatt ctggtcaaga aggagattcc ccggagcacg   1980
ctggactcgt tcatgcagcc gttccagagc acactgtggc tgctggtggg gctgtcggtg   2040
cacgtggtgg ccgtgatgct gtacctgctg gaccgcttca gccccttcgg ccggttcaag   2100
gtgaacagcg aggaggagga ggaggacgca ctgaccctgt cctcggccat gtggttctcc   2160
tggggcgtcc tgctcaactc cggcatcggg aaggcgccc cagaagctt ctcagcgcgc     2220 atcctgggca tggtgtgggc cggctttgcc atgatcatcg tggcctccta caccgccaac   2280
ctggcggcct tcctggtgct ggaccggccg gaggagcgca tcacgggcat caacgaccct   2340
cggctgagga ccccctcgga caagtttatc tacgccacgg tgaagcagag ctccgtggat   2400
atctacttcc ggcgccaggt ggagctgagc accatgtacc ggcatatgga gaagcacaac   2460
tacgagagtg cggcggaggc catccaggcc gtgagagaca acaagctgca tgccttcatc   2520
tgggactcgg cggtgctgga gttcgaggcc tcgcagaagt gcgacctggt gacgactgga   2580
gagctgtttt tccgctcggg cttcggcata ggcatgcgca aagacagccc ctggaagcag   2640
aacgtctccc tgtccatcct caagtcccac gagaatggct tcatggaaga cctggacaag   2700
acgtgggttc ggtatcagga atgtgactcg cgcagcaacg cccctgcgac ccttactttt   2760
gagaacatgg ccggggtctt catgctggta gctgggggca tcgtggccgg gatcttcctg   2820
attttcatcg agattgccta caagcggcac aaggatgctc gccggaagca gatgcagctg   2880
gcctttgccg ccgttaacgt gtggcggaag aacctgcaga gcaccggggg tggacgcggc   2940
gctttgcaaa accaaaaaga cacagtgctg ccgcgacgcg ctattgagag ggaggagggc   3000
cagctgcagc tgtgttcccg tcatagggag agctgagact cccgcccgc cctcctctgc    3060 cccctccccc gcagacagac agacagacg acggacagc ggcccggccc acgcagagcc     3120
ccggagcacc acggggtcgg gggaggagca cccccagcct ccccaggct gcgcctgccc    3180 gcccgccggt tggccggctg gccggtccac ccgtcccgg cccgcgcgt gccccagcg      3240 tgggctaac gggcgccttg tctgtgtatt tctattttgc agcagtacca tcccactgat    3300
atcacgggcc cgctcaacct ctcagatccc tcggtcagca ccgtggtgtg aggccccgg    3360 aggcgcccac ctgcccagtt agcccggcca aggacactga tgggtcctgc tgctcgggaa   3420
ggctgagggg aagcccaccc gccccagaga ctgcccaccc tgggcctccc gtccgtccgc   3480
ccgcccaccc cgctgcctgg cgggcagccc ctgctggacc aaggtgcgga ccggagcggc   3540
```

-continued

| | |
|---|---|
| tgaggacggg gcagagctga gtcggctggg cagggccgca gggcgctccg gcagaggcag | 3600 |
| ggccctgggg tctctgagca gtggggagcg ggggctaact ggccccaggc ggaggggctt | 3660 |
| ggagcagaga cggcagcccc atccttcccg cagcaccagc ctgagccaca gtggggccca | 3720 |
| tggccccagc tggctgggtc gcccctcctc gggcgcctgc gctcctctgc agcctgagct | 3780 |
| ccaccctccc ctcttcttgc ggcaccgccc acccacaccc cgtctgcccc ttgaccccac | 3840 |
| acgccggggc tggccctgcc ctcccccacg gccgtccctg acttcccagc tggcagcgcc | 3900 |
| tcccgccgcc tcgggccgcc tcctccagac tcgagagggc tgagcccctc ctctcctcgt | 3960 |
| ccggcctgca gcccagaacg ggcctccccg ggggtccccg gacgctggct cgggactgtc | 4020 |
| ttcaaccctg ccctgcacct tgggcacggg agagcgccac ccgcccgccc ccgccctcgc | 4080 |
| tccgggtgcg tgaccggccc gccaccttgt acagaaccag cactcccagg gcccgagcgc | 4140 |
| gtgccttccc cgtgcggccc gtgcgcagcc gcgctctgcc cctccgtccc cagggtgcag | 4200 |
| gcgcgcaccg cccaaccccc acctcccggt gtatgcagtg gtgatgccta aggaatgtc | 4260 |
| acgca | 4265 |

<210> SEQ ID NO 6
<211> LENGTH: 3902
<212> TYPE: DNA
<213> ORGANISM: Homo sapiens

<400> SEQUENCE: 6

| | |
|---|---|
| gtcgccgcag cgtccggacc ggaaccagcg ccgtccgcgg agccgccgcc gccgccgccg | 60 |
| ggccctttcc aagccgggcg ctcggagctg tgcccggccc cgcttcagca ccgcggacag | 120 |
| cgccggccgc gtggggctga gcccgagccc cccgcgcacg cttcagcgcc ccttccctcg | 180 |
| gccgacgtcc cgggaccgcc gctccggggg agacgtggcg tccgcagccc gcggggccgg | 240 |
| gcgagcgcag gacggcccgg aagcccgcgc gggatgcgc cgagggcccc gcgttcgcgc | 300 |
| cgcgcagagc caggcccgcg gcccgagccc atgagcacca tgcgcctgct gacgctcgcc | 360 |
| ctgctgttct cctgctccgt cgccgtgcc gcgtgcgacc ccaagatcgt caacattggc | 420 |
| gcggtgctga gcacgcggaa gcacgagcag atgttccgcg aggccgtgaa ccaggccaac | 480 |
| aagcggcacg gctcctggaa gattcagctc aatgccacct ccgtcacgca caagcccaac | 540 |
| gccatccaga tggctctgtc ggtgtgcgag gacctcatct ccagccaggt ctacgccatc | 600 |
| ctagttagcc atccacctac ccccaacgac cacttcactc ccaccccctgt ctcctacaca | 660 |
| gccggcttct accgcatacc cgtgctgggg ctgaccaccc gcatgtccat ctactcggac | 720 |
| aagagcatcc acctgagctt cctgcgcacc gtgccgccct actcccacca gtccagcgtg | 780 |
| tggtttgaga tgatgcgtgt ctacagctgg aaccacatca tcctgctggt cagcgacgac | 840 |
| cacgagggcc gggcggctca gaaacgcctg gagacgctgc tggaggagcg tgagtccaag | 900 |
| gcagagaagg tgctgcagtt tgacccaggg accaagaacg tgacgccct gctgatggag | 960 |
| gcgaaagagc tggaggcccg ggtcatcatc ctttctgcca gcgaggacga tgctgccact | 1020 |
| gtataccgcg cagccgcgat gctgaacatg acgggctccg ggtacgtgtg gctggtcggc | 1080 |
| gagcgcgaga tctcggggaa cgccctgcgc tacgcccag acggcatcct cgggctgcag | 1140 |
| ctcatcaacg gcaagaacga gtcggcccac atcagcgacg ccgtgggcgt ggtggcccag | 1200 |
| gccgtgcacg agctcctcga aaggagaaac atcaccgacc cgccgcgggg ctgcgtgggc | 1260 |
| aacaccaaca tctggaagac cgggccgctc ttcaagagag tgctgatgtc ttccaagtat | 1320 |
| gcggatgggg tgactggtcg cgtggagttc aatgaggatg gggaccggaa gttcgccaac | 1380 |

```
tacagcatca tgaacctgca gaaccgcaag ctggtgcaag tgggcatcta caatggcacc    1440
cacgtcatcc ctaatgacag gaagatcatc tggccaggcg gagagacaga gaagcctcga    1500
gggtaccaga tgtccaccag actgaagatt gtgacgatcc accaggagcc cttcgtgtac    1560
gtcaagccca cgctgagtga tgggacatgc aaggaggagt tcacagtcaa cggcgaccca    1620
gtcaagaagg tgatctgcac cgggcccaac gacacgtcgc cgggcagccc ccgccacacg    1680
gtgcctcagt gttgctacgg cttttgcatc gacctgctca tcaagctggc acggaccatg    1740
aacttcacct acgaggtgca cctggtggca gatggcaagt tcggcacaca ggagcgggtg    1800
aacaacagca caagaaggga gtggaatggg atgatgggcg agctgctcag cgggcaggca    1860
gacatgatcg tggcgccgct aaccataaac aacgagcgcg cgcagtacat cgagttttcc    1920
aagcccttca gtaccagggg cctgactatt ctggtcaaga aggagattcc ccggagcacg    1980
ctggactcgt tcatgcagcc gttccagagc acactgtggc tgctggtggg gctgtcggtg    2040
cacgtggtgg ccgtgatgct gtacctgctg gaccgcttca gccccttcgg ccggttcaag    2100
gtgaacagcg aggaggagga ggaggacgca ctgaccctgt cctcggccat gtggttctcc    2160
tggggcgtcc tgctcaactc cggcatcggg aaggcgccc ccagaagctt ctcagcgcgc    2220
atcctgggca tggtgtgggc cggctttgcc atgatcatcg tggcctccta caccgccaac    2280
ctggcggcct tcctggtgct ggaccggccg gaggagcgca tcacgggcat caacgaccct    2340
cggctgagga ccccctcgga caagtttatc tacgccacgg tgaagcagag ctccgtggat    2400
atctacttcc ggcgccaggt ggagctgagc accatgtacc ggcatatgga gaagcacaac    2460
tacgagagtg cggcggaggc catccaggcc gtgagagaca acaagctgca tgccttcatc    2520
tgggactcgg cggtgctgga gttcgaggcc tcgcagaagt gcgacctggt gacgactgga    2580
gagctgtttt tccgctcggg cttcggcata ggcatgcgca aagacagccc ctggaagcag    2640
aacgtctccc tgtccatcct caagtcccac gagaatggct tcatggaaga cctggacaag    2700
acgtgggttc ggtatcagga atgtgactcg cgcagcaacg cccctgcgac ccttactttt    2760
gagaacatgg ccggggtctt catgctggta gctgggggca tcgtggccgg gatcttcctg    2820
attttcatcg agattgccta caagcggcac aaggatgctc gccggaagca gatgcagctg    2880
gcctttgccg ccgttaacgt gtggcggaag aacctgcagc agtaccatcc cactgatatc    2940 acgggccccgc tcaacctctc agatccctcg gtcagcaccg tggtgtgagg cccccggagg    3000
cgcccacctg cccagttagc ccggccaagg acactgatgg gtcctgctgc tcgggaaggc    3060
ctgagggaag cccacccgcc ccagagactg cccaccctgg gcctcccgtc cgtccgcccg    3120
cccaccccgc tgcctggcgg gcagcccctg ctggaccaag gtgcggaccg gagcggctga    3180
ggacggggca gagctgagtc ggctgggcag ggccgcaggg cgctccggca gaggcagggc    3240
cctggggtct ctgagcagtg gggagcgggg gctaactggc cccaggcgga ggggcttgga    3300
gcagagacgg cagccccatc cttcccgcag caccagcctg agccacagtg gggcccatgg    3360
ccccagctgg ctgggtcgcc cctcctcggg cgcctgcgct cctctgcagc ctgagctcca    3420
ccctcccctc ttcttgcggc accgccacc cacacccgt ctgcccttg acccacacg    3480 ccggggctgg ccctgccctc ccccacggcc gtccctgact tccagctgg cagcgcctcc    3540 cgccgcctcg ggccgcctcc tccagactcg agagggctga gccctcctc tcctcgtccg    3600 gcctgcagcc cagaacgggc ctccccgggg gtccccggac gctggctcgg gactgtcttc    3660
aaccctgccc tgcaccttgg gcacgggaga gcgccaccg cccgcccccg ccctcgctcc    3720
gggtgcgtga ccggcccgcc accttgtaca gaaccagcac tcccagggcc cgagcgcgtg    3780
```

| | |
|---|---|
| ccttccccgt gcggcccgtg cgcagccgcg ctctgcccct ccgtcccag ggtgcaggcg | 3840 |
| cgcaccgccc aaccccacc tcccggtgta tgcagtggtg atgcctaaag gaatgtcacg | 3900 |
| ca | 3902 |

What is claimed is:

1. A method of diagnosing an autoimmune encephalitis in a subject, comprising the steps of obtaining a serum or cerebrospinal fluid (CSF) sample from said subject; and testing said sample for an antibody to an NR1 subunit of an N-methyl D-aspartate (NMDA) receptor, whereby the presence of said antibody in said sample indicates said autoimmune encephalitis, thereby diagnosing said autoimmune encephalitis in said subject, wherein said NR1 subunit comprises the amino acid sequence set forth in SEQ ID NO: 1.

2. The method of claim 1, whereby said antibody binds to extra cellular N-terminal domain of said NR1 subunit.

3. The method of claim 2, whereby said antibody binds to a region comprising amino acids 25-380 of SEQ ID NO: 1.

4. The method of claim 2, whereby said antibody binds to a region comprising a functional fragment of amino acid sequence of SEQ ID NO: 1.

5. The method of claim 1, whereby said autoimmune encephalitis is an anti-NMDA receptor encephalitis.

6. The method of claim 1, whereby said autoimmune encephalitis is associated with pathological symptoms.

7. The method of claim 6, whereby the symptoms are seizures; psychiatric symptoms; abnormality in cognition and behavior; a movement disorder or abnormal movements; a decreased level of consciousness; hypoventilation; amnesia or a memory deficit; or a combination thereof.

* * * * *

UNITED STATES PATENT AND TRADEMARK OFFICE
CERTIFICATE OF CORRECTION

PATENT NO. : 7,972,796 B2
APPLICATION NO. : 12/277252
DATED : July 5, 2011
INVENTOR(S) : Josep Dalmau et al.

Page 1 of 1

It is certified that error appears in the above-identified patent and that said Letters Patent is hereby corrected as shown below:

Title Page, Item (73)
The Assignee should read:

The Trustees of the University of Pennsylvania, Philadelphia, PA
The Children's Hospital of Philadelphia, Philadelphia, PA

Signed and Sealed this
Twelfth Day of June, 2012

David J. Kappos
*Director of the United States Patent and Trademark Office*